United States Patent
Phillips et al.

(10) Patent No.: US 11,235,154 B2
(45) Date of Patent: Feb. 1, 2022

(54) APPARATUS AND METHODS FOR MAINTAINING PHYSIOLOGICAL FUNCTIONS

(71) Applicant: THE UNIVERSITY OF BRITISH COLUMBIA, Vancouver (CA)

(72) Inventors: Aaron Phillips, Calgary (CA); Andrei Krassioukov, Vancouver (CA); Jordan Squair, Surrey (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 339 days.

(21) Appl. No.: 16/486,788

(22) PCT Filed: Feb. 16, 2018

(86) PCT No.: PCT/CA2018/050184
§ 371 (c)(1),
(2) Date: Aug. 16, 2019

(87) PCT Pub. No.: WO2018/148844
PCT Pub. Date: Aug. 23, 2018

(65) Prior Publication Data
US 2020/0230417 A1    Jul. 23, 2020

Related U.S. Application Data

(60) Provisional application No. 62/581,305, filed on Nov. 3, 2017, provisional application No. 62/470,468, filed (Continued)

(51) Int. Cl.
*A61N 1/36* (2006.01)
*A61N 1/04* (2006.01)
(Continued)

(52) U.S. Cl.
CPC ........ *A61N 1/36117* (2013.01); *A61N 1/0456* (2013.01); *A61N 1/0551* (2013.01);
(Continued)

(58) Field of Classification Search
CPC ............ A61N 1/36117; A61N 1/36031; A61N 1/36034; A61N 1/0456; A61N 1/0551;
(Continued)

(56) References Cited

U.S. PATENT DOCUMENTS 6,058,331 A    5/2000  King
7,647,115 B2 *  1/2010  Levin ................. A61B 18/1492
                                                    607/44
(Continued)

FOREIGN PATENT DOCUMENTS

JP    2004-065529 A    3/2004
JP       6132856 B2    4/2017
(Continued)

OTHER PUBLICATIONS

Phillips, A. A. et al., "Contemporary Cardiovascular Concerns after Spinal Cord Injury: Mechanisms, Maladaptations, and Management", Journal of Neurotrauma 32:1927-1942, Dec. 15, 2015.
(Continued)

*Primary Examiner* — Mark W. Bockelman
(74) *Attorney, Agent, or Firm* — McCoy Russell LLP

(57) ABSTRACT

A device and algorithm for controlling an autonomic function in an individual. In particular, a controller device that utilizes physiological measurements (such as blood pressure) to regulate spinal cord electrical stimulation to stabilize blood pressure. A control interface and algorithm for controlling an autonomic function in a subject. In particular, an algorithm that utilizes physiological measurements (such as blood pressure) to regulate spinal cord electrical stimulation to stabilize blood pressure.

28 Claims, 20 Drawing Sheets

Related U.S. Application Data on Mar. 13, 2017, provisional application No. 62/460,224, filed on Feb. 17, 2017.

(51) Int. Cl.
*A61N 1/05* (2006.01)
*A61B 5/021* (2006.01)

(52) U.S. Cl.
CPC ..... *A61N 1/36031* (2017.08); *A61N 1/36034* (2017.08); *A61N 1/36057* (2013.01); *A61N 1/36139* (2013.01); *A61B 5/021* (2013.01)

(58) Field of Classification Search
CPC ............ A61N 1/36057; A61N 1/36139; A61N 1/36135; A61B 5/021; A61B 5/4836
See application file for complete search history.

(56) References Cited

U.S. PATENT DOCUMENTS

| | | | |
|---|---|---|---|
| 8,332,047 B2 * | 12/2012 | Libbus | A61N 1/36053 607/117 |
| 8,626,300 B2 | 1/2014 | Demarais et al. | |
| 8,740,825 B2 | 6/2014 | Ehrenreich et al. | |
| 9,205,261 B2 | 12/2015 | Kim et al. | |
| 9,248,291 B2 | 2/2016 | Mashiach | |
| 9,272,139 B2 | 3/2016 | Hamilton et al. | |
| 9,314,630 B2 | 4/2016 | Levin et al. | |
| 2007/0027495 A1 | 2/2007 | Gerber | |
| 2011/0202107 A1 | 8/2011 | Sunagawa et al. | |
| 2013/0237948 A1 | 9/2013 | Donders et al. | |
| 2013/0289650 A1 | 10/2013 | Karlsson et al. | |
| 2013/0296965 A1 | 11/2013 | Mokelke et al. | |
| 2016/0121121 A1 | 5/2016 | Mashiach | |
| 2017/0007320 A1 | 1/2017 | Levin et al. | |
| 2017/0056661 A1 | 3/2017 | Lin et al. | |

FOREIGN PATENT DOCUMENTS

| | | |
|---|---|---|
| JP | 2017-104685 A | 6/2017 |
| WO | 2017146659 A1 | 8/2017 |

OTHER PUBLICATIONS

Anderson, K.D., Targeting Recovery: Priorities of the Spinal Cord-Injured Population, Journal of Neurotrauma, vol. 21, No. 10, 2004, pp. 1371-1383.

Wan, D. et al., "Life-threatening outcomes associated with autonomic dysreflexia: A clinical review", The Journal of Spinal Cord Medicine, vol. 37, pp. 2-10, 2014.

Krassioukov, A., et al., "A Systematic Review of the Management of Autonomic Dysreflexia After Spinal Cord Injury", Archives of Physical Medicine and Rehabilitation 2009 90(4):682-695.

Krassioukov, A. et al., "A Systematic Review of the Management of Orthostatic Hypotension Following Spinal Cord Injury", Arch Phys Med Rehabil 2009; 90(5):876-885.

Phillips, A.A. et al., "Perturbed and spontaneous regional cerebral blood flow responses to changes in blood pressure after high level spinal cord injury: the effect of midodrine", Journal of Applied Physiology (1985) 2014;116(6):645-653.

Phillips, A.A. et al., "Regional neurovascular coupling and cognitive performance in those with low blood pressure secondary to high-level spinal cord injury: improved by alpha-1 agonist midodrine hydrochloride", Journal of Cerebral Blood Flow & Metabolism (2014);34:794-801.

* cited by examiner

Uninjured

APPARATUS AND METHODS FOR MAINTAINING PHYSIOLOGICAL FUNCTIONS

CROSS-REFERENCE TO RELATED APPLICATIONS

This application claims priority from U.S. Application No. 62/460,224 filed 17 Feb. 2017, U.S. Application No. 62/470,468 filed 13 Mar. 2017, and U.S. Application No. 62/581,305 filed 3 Nov. 2017. For purposes of the United States, this application claims the benefit under 35 U.S.C. § 119 of U.S. Application No. 62/460,224 filed 17 Feb. 2017 and entitled SERVO-CONTROLLED DEVICE TO MAINTAIN PHYSIOLOGICAL FUNCTIONING, U.S. Application No. 62/470,468 filed 13 Mar. 2017 entitled SERVO CONTROLLED INTERFACE TO CONTROL ELECTRICAL STIMULATION FOR RESTORING PHYSIOLOGICAL FUNCTIONING, and U.S. Application No. 62/581,305 filed 3 Nov. 2017 entitled SERVO CONTROLLED INTERFACE TO CONTROL ELECTRICAL STIMULATION FOR RESTORING PHYSIOLOGICAL FUNCTIONING, all of which are hereby incorporated herein by reference for all purposes.

FIELD OF THE INVENTION

The present invention generally relates to the field of bionic interphases. More specifically, the invention relates to machine control of physiological functions by way of controlled stimulation (e.g. electrical stimulation). The invention has example application for treating hypotension (low blood pressure) in subjects affected by spinal cord injury.

BACKGROUND OF THE INVENTION

Spinal cord injury (SCI) results in disconnection of some, most, or all descending sympathetic pathways that carry signals responsible for regulating blood pressure. When arterial blood pressure drops or increases following SCI, the spinal cord neurons responsible for blood pressure control no longer have the capacity to maintain blood pressure at a normal physiological level. This disconnection of sympathetic pathways can lead to a situation where blood vessels do not maintain appropriate tone (e.g. the blood vessels can become dilated). As a result subjects affected by SCI can suffer from extreme hypotension (very low blood pressure). Large amounts of blood may pool in subjects' legs and gut.

Individuals with SCI are often unable to regulate their blood pressure and typically experience a very low arterial blood pressure at rest, during exercise and/or when assuming a seated or standing position. This hypotension can lead to dizziness, disorientation, reduction in cognitive functioning, loss of consciousness and a predisposition to strokes and heart attacks. On the other hand, dangerous elevations in blood pressure (hypertension) can also result from SCI. Hypertension can lead to heart attacks, strokes, and sub-clinical vascular consequences.

Despite widespread misconceptions, autonomic and cardiovascular dysfunctions following SCI are a top health priority (above walking again) and are a main cause of death for individuals with SCI. One primary autonomic issue after high-level SCI (i.e., above the 6th thoracic segment) is orthostatic hypotension, which is clinically-defined as a ≥20 mmHg decrease in systolic blood pressure and/or a 10 mmHg decrease in diastolic blood pressure when assuming the upright posture.

Another critical autonomic issue after SCI is autonomic dysreflexia, which is associated with potentially life threatening elevations in blood pressure, due to afferent input activating sympathetic circuitry located caudally on the spinal cord to the location of the SCI. Clinically, autonomic dysreflexia is defined as elevations in systolic blood pressure of 20 mmHg or more.

Currently, the main options for managing blood pressure lability after SCI are pharmacological agents that either can increase or decrease blood pressure. However, most pharmacological tools available for managing orthostatic hypotension and autonomic dysreflexia have significant side effects, as well as a delayed onset of action (at least 10 minutes for drugs to manage high blood pressure, and 60 minutes or more for drugs that manage low blood pressure), and therefore are sub-optimal for managing transient (seconds), but drastic, changes in blood pressure that occur after SCI and other neurological conditions such as multiple sclerosis, autonomic failure, autonomic neuropathy, as well as cancer of the neurological tissue. Importantly, the effects of some of the antihypertensive drugs (e.g. for management of autonomic dysreflexia) can result in a significant decrease in arterial blood pressure, below the desired level, which can last for hours and requires monitoring and further management. As such, pharmacological intervention is often ineffective and can predispose an individual with SCI to extreme changes in blood pressure. Alternative options for controlling blood pressure without the adverse effects inherent to current pharmacological therapies are therefore needed.

The following references provide background to the technology described in the present application:

1. Phillips A A, Krassioukov A V. Contemporary cardiovascular concerns after spinal cord injury: Mechanisms, maladaptations & management. Journal of Neurotrauma. 2015; 32:1927-42.
2. Anderson K D. Targeting recovery: priorities of the spinal cord-injured population. Journal of Neurotrauma. 2004; 21:1371-1383.
3. Wan D, Krassioukov A V. Life-threatening outcomes associated with autonomic dysreflexia: A clinical review. The journal of spinal cord medicine. 2014; 37:2-10.
4. Krassioukov A, Warburton D E, Teasell R, Eng J J. A Systematic Review of the Management of Autonomic Dysreflexia After Spinal Cord Injury. Archives of physical medicine and rehabilitation. 2009; 90:682-695.
5. Krassioukov A, Eng J J, Warburton D E, Teasell R. A systematic review of the management of orthostatic hypotension after spinal cord injury. Arch Phys Med Rehabil. 2009; 90:876-885.
6. Phillips A A, Krassioukov A V, Ainslie P N, Warburton D E R. Perturbed and spontaneous regional cerebral blood flow responses to changes in blood pressure after high level spinal cord injury: the effect of midodrine. Journal of applied physiology (Bethesda, Md.: 1985). 2014; 116:645-653.
7. Phillips A A, Warburton D E R, Ainslie P N, Krassioukov A V. Regional neurovascular coupling and cognitive performance in those with low blood pressure secondary to high-level spinal cord injury: improved by alpha-1 agonist midodrine hydrochloride. Journal of Cerebral Blood Flow & Metabolism. 2014; 34:794-801.

Patent literature in the general field of the present technology includes:

- US20110202107A1 2011 Aug. 18 BLOOD PRESSURE STABILIZATION SYSTEM USING TRANSDERMAL STIMULATION describes electric stimulation apparatus for treating hypotension of patients with spinal cord injury and a method for treating hypotension. The apparatus comprises: a blood pressure measuring means for continuously measuring a blood pressure of a subject; an electric current application means for intermittently applying an electric current to skin of the subject; and a control means for controlling the electric current application means so as to maintain the blood pressure at a predetermined target blood pressure value by activating the electric current application means when the subject blood pressure is equal to or less than the target blood pressure value.
- JP2004065529A 2004 Mar. 4 BLOOD PRESSURE CONTROLLING APPARATUS describes a blood pressure controlling apparatus which controls a blood pressure in place of a blood pressure control center of the brain without relying on administration of a hypertensor into a vein or blood transfusion. The apparatus has a blood pressure sensor for detecting a blood pressure value of a living body and an electric stimulation part outputting stimulative electricity to be given to the spinal sympathetic nervous system of the living body. A stimulation frequency control part which calculates the stimulation frequency of a stimulative electricity that needs to be given to the spinal sympathetic nervous system of the living body for raising the blood pressure value of the living body to a target set value. A pulse current output part which outputs the stimulative electricity of the stimulation frequency calculated by the control part
- US20130237948A1 2013 Sep. 12 DEVICES FOR REGULATION OF BLOOD PRESSURE AND HEART RATE describe devices for regulation of blood pressure and heart rate which involve applying electrical treatment signals selected to at least partially block nerve impulses, or in some embodiments, to augment nerve impulses. The apparatus provides a therapy program to provide a downregulating signal to one or more nerves including renal artery, renal nerve, vagus nerve, celiac plexus, splanchnic nerve, cardiac sympathetic nerves, and spinal nerves originating between T10 to L5. In embodiments, the apparatus provides a therapy program to provide an upregulating signal to one or more nerves including a glossopharyngeal nerve and/or a tissue containing baroreceptors.
- US20130289650A1 2013 Oct. 31 Neuromodulation for Hypertension Control describes use of neuromodulation for controlling hypertension and other cardiorenal disorders of a patient. A neuromodulation device is configured to be delivered to a patient's body and to apply an electric activation to decrease renal sympathetic hyperactivity of the patient based on monitored blood pressure of the patient, substantially without thermal energization of the patient's body by applying the electric activation. The electric activation may also depend on monitored blood volume of the patient. A feedback control module may be used to provide feedback control information for adjusting the electric activation based on the monitored blood pressure and volume of the patient.
- WO2017146659A1 2017 Aug. 31 A SYSTEM FOR DECREASING THE BLOOD PRESSURE describes a blood pressure decreasing system that decreases blood pressure of a patient by non-invasively blocking the sympathetic innervation of the kidney;
- US20170056661A1 2017 Mar. 2 METHOD OF REDUCING RENAL HYPERTENSION AND COMPUTER-READABLE MEDIUM describes a method of reducing renal hypertension by applying stimulation to a target zone of an organism using an electronic stimulation device.
- US20170007320A1 2017 Jan. 12 RENAL NEUROMODULATION FOR TREATMENT OF PATIENTS and U.S. Pat. No. 9,314,630B2 2016 Apr. 19 describes a method and apparatus for treatment of heart failure, hypertension and renal failure by stimulating the renal nerve.
- U.S. Pat. No. 8,740,825B2 2014 Jun. 3 Methods and devices for treating hypertension describes devices, systems and methods which control blood pressure and nervous system activity by stimulating baroreceptors and/or nerves to reduce blood pressure.
- US20130296965A1 2013 Nov. 7 METHOD FOR BLOOD PRESSURE MODULATION USING ELECTRICAL STIMULATION OF THE CORONARY BARORECEPTORS describes apparatus comprising a first stimulation circuit and a control circuit. The stimulation circuit is configured to be electrically coupled to a first electrode assembly that is configured to deliver electrical sub-myocardial activation stimulation to a coronary baroreceptor from a location within a left atrial appendage of a heart.

There remains a need for apparatus and methods that can help people who are suffering from dysregulated autonomic functions as a result of SCI.

SUMMARY

The present disclosure describes technology that has a number of aspects. These aspects may be applied in combination with one another but may also have individual application. These aspects include, without limitation:

A device and algorithm for controlling an autonomic process in a subject using electrical stimulation. The device and algorithm of the present disclosure are based on the surprising discovery that the electrical excitation of spinal cord circuitry caudal to SCI can control the activity of disconnected sympathetic circuitry to regulate blood pressure.

A method performed by a device for generating control signals for a stimulation device.

Methods for regulating blood pressure in subjects affected by SCI. The methods may be effective to alleviate hypotension in such subjects.

Methods for controlling stimulation delivery devices to generate stimulation that may be effective for controlling one or more autonomic functions in a subject.

A system and methods for controlling one or more autonomic functions in a subject.

A method for medical treatment of a subject affected by SCI.

A device according to an example embodiment comprises a processing unit and circuitry that may be configured such that the device may act as an interface between 1) a physiological monitor (e.g., a blood pressure monitor), and 2) a stimulation device (e.g. an electrical stimulation assembly). The device may interface with a variety of physiological monitors and stimulation devices. The device may optionally be connected wirelessly to either or both of the physiological monitor and the stimulation device.

The device may be configured to receive and analyze information from the physiological monitor. The device may be configured to direct an electrical stimulation assembly to transmit output electrical stimulation (or another type of stimulation device to generate other stimulation). The output electrical stimulation may be epidural, for example. The device may cause the stimulation output to increase or decrease depending on the information received from the physiological monitor. The stimulation output may remain constant depending on the information received from the physiological monitor. The stimulation output may improve control of an autonomic function such as blood pressure. The device may operate by feedback control.

The device may be for use in a subject having dysregulated blood pressure. The dysregulated blood pressure may be due to SCI or other neurological conditions such as multiple sclerosis, autonomic failure, autonomic neuropathy, as well as cancer of the neurological tissue. The output electrical stimulation may raise or lower blood pressure in a subject with dysregulated blood pressure according to a set of predetermined parameters. The output electrical stimulation may be useful for controlling hypotension in a subject affected by dysregulated blood pressure.

Another aspect of the invention provides apparatus for controlling blood pressure in a subject. The apparatus comprises an input for receiving a BP signal indicative of a blood pressure measurement and a feedback control circuit connected to receive the BP signal from the input and to deliver a stimulation control signal to an output. The feedback control circuit is configured to: compare the blood pressure measurement to a target blood pressure range, if the comparison indicates that the blood pressure measurement is below the target blood pressure range increase a level of the stimulation control signal until the blood pressure measurement is in the target blood pressure range; and if the comparison indicates that the blood pressure measurement is above the target blood pressure range decrease a level of the stimulation control signal until the blood pressure measurement is in the target blood pressure range.

Another aspect of the invention provides a method for operating apparatus to control a subject's blood pressure. The method comprises: receiving at the apparatus a signal containing a blood pressure measurement indicative of the subject's blood pressure and comparing the blood pressure measurement to a predetermined target range stored in a data store accessible to the apparatus If the comparison indicates that the blood pressure measurement is below the target blood pressure range the method increases a level of a stimulation control signal until the blood pressure measurement is in the target blood pressure range. If the comparison indicates that the blood pressure measurement is above the target blood pressure range the method decreases the level of the stimulation control signal until the blood pressure measurement is in the target blood pressure range.

Another aspect of the invention provides apparatus for controlling one or more autonomous functions in a subject. The apparatus comprises: an input for receiving a monitor signal indicative of a parameter value and a feedback control circuit connected to receive the monitor signal from the input and to deliver a stimulation control signal to an output. The feedback control circuit is configured to: compare the parameter value to a target range. If the comparison indicates that the parameter value is below the target range the control circuit increases a level of the stimulation control signal until the parameter value is in the target range; and if the comparison indicates that the parameter value is above the target range the control circuit decreases a level of the stimulation control signal until the parameter value is in the target range.

Another aspect of the invention provides a method for operating apparatus to control one or more autonomous functions of a subject. The method comprises: receiving at the apparatus a signal containing a monitor measurement indicative of a parameter value; comparing the parameter value to a predetermined target range stored in a data store accessible to the apparatus; and, if the comparison indicates that the parameter value is below the target range increasing a level of a stimulation control signal until the parameter value is in the target parameter value range; and if the comparison indicates that the parameter value is above the target range decreasing the level of the stimulation control signal until the parameter value is in the target range.

Another aspect of the invention provides the use of any apparatus as described herein for controlling an autonomic function of a person affected by SCI.

Another aspect of the invention provides a method for medical treatment of subjects who have dysfunctional regulation of blood pressure or another autonomic function as a result of SCI (broadly interpreted as any condition which impairs operation of descending sympathetic pathways that normally facilitate control of autonomic functions). The method involves regulating the autonomic function by applying stimulation to structures in the lower back caudal to the SCI. The stimulation may comprise stimulating dorsal roots, dorsal afferent fibres and/or intraspinal structures that are connected directly or indirectly to sympathetic preganglionic neurons that affect the function being controlled.

The stimulation may be provided, for example, in the form of electrical stimulation. The electrical stimulation may be delivered to the dorsal aspect of the spinal cord of the subject, for example by way of an implanted electrode structure. The electrode structure is located caudal to the SCI, for example over the lumbosacral spinal cord segments (e.g. at T11-L1 vertebral levels). The method may involve feedback control of the stimulation based on monitoring a parameter that represents activity of the function being regulated. For example, the function may be blood pressure regulation and the parameter may be a blood pressure measured by a blood pressure monitor.

Further aspects of the invention and features and combinations of features of example embodiments are illustrated in the accompanying drawings and described below.

BRIEF DESCRIPTION OF THE DRAWINGS

The accompanying drawings illustrate non-limiting examples of the present technology.

DETAILED DESCRIPTION

Throughout the following description, specific details are given as examples in an attempt to impart a thorough understanding of the invention. However, the invention may be practiced in various forms not all of which embody such details. In other instances, well known elements have not been shown or described in detail to avoid unnecessarily obscuring the invention. Accordingly, the specification and drawings are to be regarded in an illustrative, rather than a restrictive sense.

One aspect of the present technology provides devices for automated control of a dysregulated autonomic function (such as blood pressure, bladder control and bowel control) in subjects. Such devices have particular application in treating subjects affected by SCI or other neurological conditions such as multiple sclerosis, autonomic failure, autonomic neuropathy, or cancer of the neurological tissue which impair operation of descending sympathetic pathways that normally facilitate control of autonomic functions.

Figure 1:
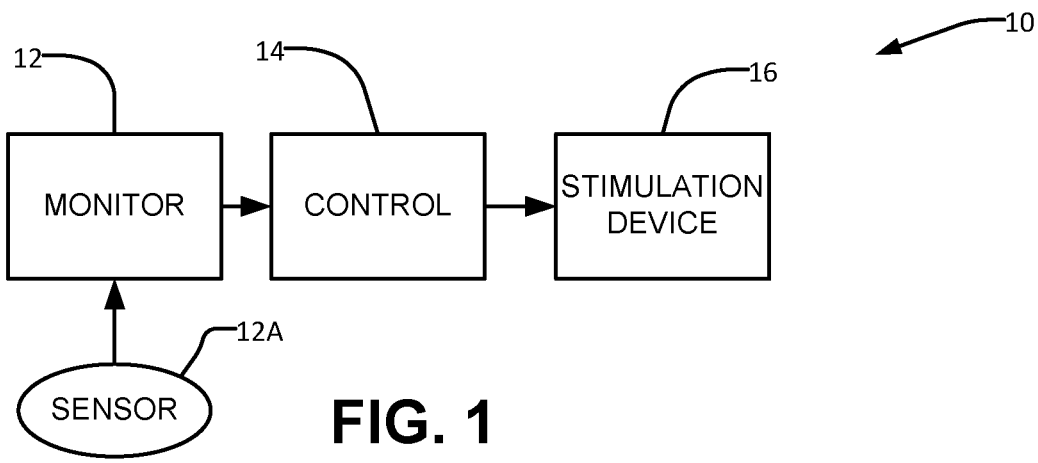
FIG. 1 is a block diagram illustrating apparatus according to an example embodiment.

FIG. 1 illustrates example apparatus 10 according to one embodiment. Apparatus 10 includes a monitor 12 which measures a parameter of an autonomic function of the subject. The parameter may, for example, comprise the subject's blood pressure, bladder volume, bladder pressure, etc. Monitor 12 includes a sensor 12A of a type suitable for the autonomic function being monitored. Sensor 12A may comprise a blood pressure sensor such as a cuff, an arterial pressure sensor, an optical biometric sensor etc. a bladder monitor such as a near infrared sensor (NIRS), an EMG sensor (such as a surface or needle type EMG sensor) for example. An EMG sensor may, for example, be located to measure activity of a muscle such as a muscle that controls the anal sphincter.

Control circuit 14 is configured to receive and analyze information from monitor 12. In the FIG. 1 embodiment control circuit 14 receives a signal indicating the parameter value from monitor 12. The information may comprise, for example, a parameter value such as a diastolic blood pressure, a systolic blood pressure, a diastolic blood pressure and a systolic blood pressure, a blended blood pressure value, a bladder volume, a bladder pressure, a measure of muscle tension or relaxation or the like. Control circuit 14 determines whether the measured parameter value is acceptable, too high or too low. In response to the determination, control circuit 14 controls a stimulation device 16 to apply stimulation to the patient.

The stimulation may be in any of one or more different forms. For example, the stimulation delivered by stimulation device 16 may comprise one or more of:
Electrical signals;
Optical signals;
Magnetic signals;
Optogenetic manipulation;
Chemogenetic manipulation;
Delivery of a chemical agent;
Thermal signals; etc.

In preferred cases the stimulation is delivered to the dorsal aspect of the spinal cord of a subject. The stimulation may affect dorsal roots, dorsal afferent fibres and/or intraspinal structures that are connected directly or indirectly to sympathetic preganglionic neurons that affect the function being controlled. The stimulation is preferably delivered caudal to a location of an SCI which has interrupted autonomic control of the function. While the inventors do not intend to be bound by any theory of operation, it is thought that stimulation delivered to affect dorsal roots, dorsal afferent fibres and/or intraspinal structures may be processed by neural structures in the spinal cord, particularly structures caudal to the SCI to cause signals on efferent nerves that, in turn, affect operation of the function being controlled.

Control circuit 14 may be integrated with monitor 12 and/or stimulation device 16 or may be provided as a stand-alone device that acts as an interface between monitor 12 and stimulation device 16. Where control circuit 14 is provided as a part of a stand-alone device, the device may comprise a specialized device or a programmed general purpose device such as a stand-alone CPU, microprocessor, mobile phone, tablet, etc.

The following sections provide more detailed example applications of the present technology to the control of blood pressure in subjects affected by SCI. It should be appreciated that all of these examples may be readily adapted for control of another function by replacement of a blood pressure monitor with a monitor that detects a parameter relevant to the function to be controlled and by suitable choice of stimulation. These examples describe electrical stimulation but may be adapted to use other types of stimulation by suitable choice of an alternative stimulation device.

Figure 1A:
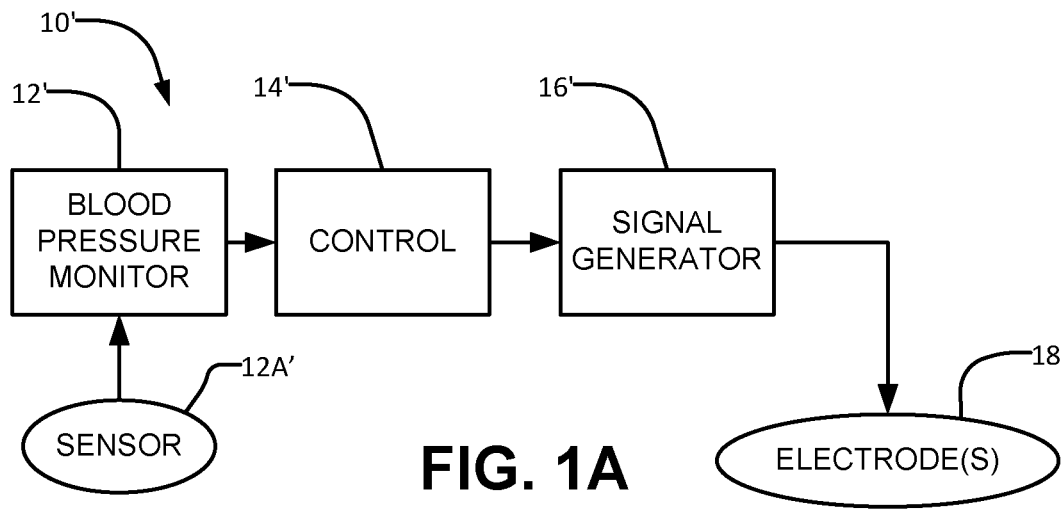
FIG. 1A is a schematic illustration showing blood pressure control apparatus according to an example implementation.

FIG. 1A illustrates a more specific example apparatus 10'. Apparatus 10' is operable to control blood pressure of a subject. Apparatus 10' includes a blood pressure monitor 12' which measures the subject's blood pressure by way of a sensor 12A', a control circuit 14' which receives a signal indicating the subject's blood pressure from blood pressure monitor 12' and determines whether the blood pressure is acceptable, too high or too low.

Control circuit 14' is configured to receive and analyze information from blood pressure monitor 12'. The information may comprise, for example, a diastolic blood pressure, a systolic blood pressure, or a diastolic blood pressure and a systolic blood pressure. In response to the determination, control circuit 14' controls a stimulation circuit 16' to apply signals to the patient by way of electrode(s) 18.

Control circuit 14' may control any of a wide range of characteristics of electrical signals to be delivered by way of electrodes 18. For example, control circuit 14' may control one or any combination of: electrical stimulation voltage, the frequency of electrical stimulation, the pulse width of stimulation, the amplitude of stimulation, or any permutation of these factors or other electrical characteristics. The result is that apparatus 10' delivers electrical stimulation based on information received from the blood pressure monitor.

The signals delivered by control circuit 14 or 14' may, for example, comprise commands to be executed by a processor or other device in stimulation circuit 16' and/or parameters to be used by simulation circuit 16' in generating the stimulation and/or a waveform for stimulation signals in analog or digital form and/or a selection of a program to be used by stimulation circuit 16' in generating the stimulation.

Control circuit 14 or 14' may, for example, comprise one or any combination of: a programmed data processor (such as a microprocessor, industrial controller, embedded processor or the like), hardwired logic circuits and/or configurable logic circuits. Control circuit 14 comprises or has access to a data store or data registers which can contain parameters which affect control of the subject's blood pressure.

Embodiments of the invention including various designs for control circuit 14 or 14' may be implemented using any of:
  specifically designed hardware,
  configurable hardware,
  programmable data processors configured by the provision of software (which may optionally comprise "firmware") capable of executing on the data processors,
  special purpose computers or data processors that are specifically programmed, configured, or constructed to perform one or more steps in a method as explained in detail herein and/or
  combinations of two or more of these.

Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit 14 may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

Figure 1B:
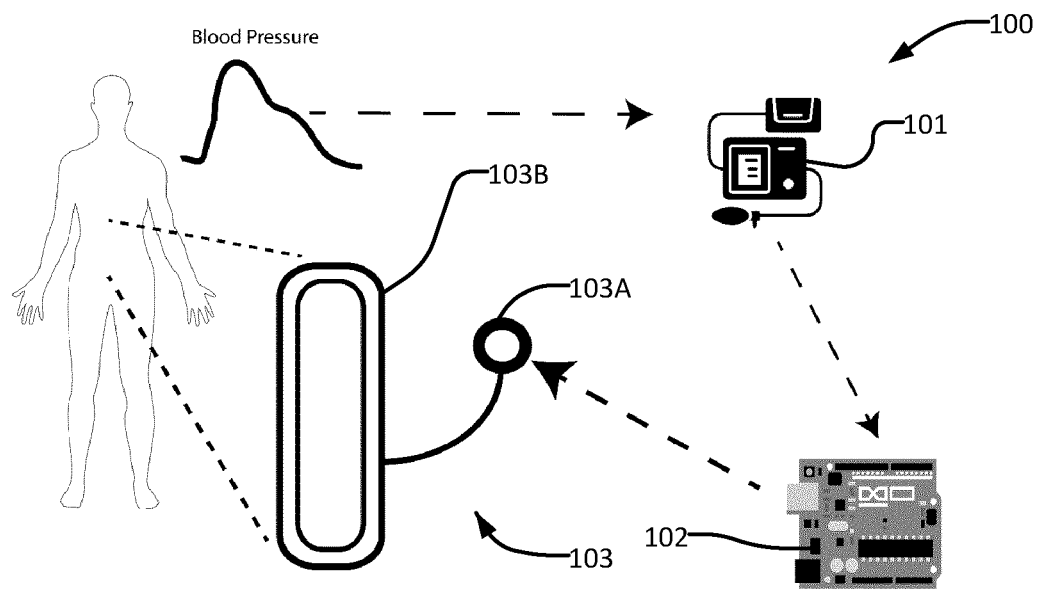
FIG. 1B is a schematic illustration showing blood pressure control apparatus according to another example implementation.
Figure 1C:
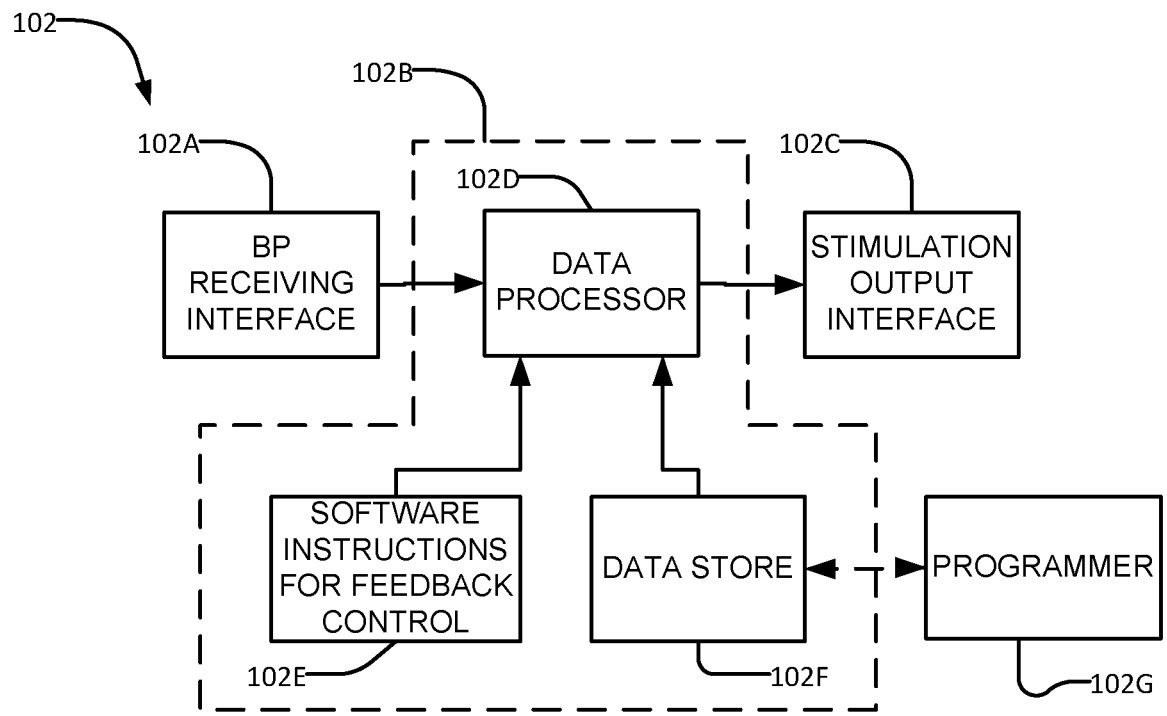
FIG. 1C is a block diagram of an example interface device.

FIG. 1B shows example apparatus 100 in which control circuit 14 is part of a device 102 that acts as an interface between a standalone blood pressure monitor 101 and an electrical stimulation assembly 103. Device 102 may, for example, comprise:
  A processing unit
  Circuitry which may comprise:
  A receiving module
  A transmitting module
  A feedback control module
  A memory for storing blood pressure and stimulation settings FIG. 1C is a block diagram illustrating a possible construction for device 102. In this example, device 102 comprises a blood pressure receiving interface 102A, a feedback control circuit 102B and a stimulation output interface. Feedback control circuit 102B may have any of a wide variety of constructions. In this example, feedback control circuit 102B comprises a data processor 102D which executes instructions in a program store 102E. The instructions cause the processor to process blood pressure readings received by way of interface 102A and to determine stimulation settings. Parameters may be written to data store 102F, for example, by way of a programmer 102G or remote control/programmer that interfaces to device 102 by way of a wired or wireless data connection. Parameters stored in a data store 102F may be applied in determination of the stimulation settings. The stimulation settings are output to a stimulation system by way of interface 102C.

Device 102 may interface with blood pressure monitor 101 and electrical stimulation assembly 103 in any suitable manner including wirelessly. Interfaces 102A and 102C may, for example, comprise:
  wireless data interfaces such as WiFi, Bluetooth, or the like;
  wired or optical data interfaces.

In some embodiments both of interfaces 102A and 102C are provided by the same physical hardware.

Blood pressure monitor 101 may comprise any blood pressure measuring device. For example, blood pressure monitor 101 may be provided by any of:
  a beat-by-beat finometer device.
  a device that operates by discrete brachial auscultation methods,
  a wrist watch with blood pressure measurement circuitry,
  a phothoplethymography device,
  a tonometer,
  an intra-arterial blood pressure measuring cannula.

Electrical stimulation assembly 103 may be provided by any suitable stimulation assembly capable of providing spinal cord electrical stimulation as described herein. For example, electrical stimulation assembly 103 may comprise a commercially-available electrical stimulation device. The electrical stimulation assembly may, for example, provide epidural spinal cord stimulation.

The electrical stimulation assembly may comprise one or more stimulation electrodes 103B connected to an electrical pulse generator 103A. In some embodiments electrodes 130B are provided on an implantable device. The implantable device may, for example, comprise a commercially available electrode paddle. A wide range of suitable implantable electrode structures are commercially available. These electrode structures differ in the number of electrodes provided (configurations which include 8, 16, or 32 electrodes and associated contact leads are common). Such structures may be designed for surgical or percutaneous application and are dimensioned to fit within the dimensions of the spinal canal at the appropriate spinal segment.

Device 102 may be programmed to decide, based on pre-determined criteria, the appropriate stimulation output to be supplied by electrical stimulation assembly 103. The criteria may, for example, include one or more of:
  one or more parameters that indicate what blood pressure is desirable for a subject;
  one or more parameters that indicate how the subject responds to stimulation from electrical stimulation assembly 103;

one or more parameters that specify characteristics of a stimulation signal (e.g. frequency, current, pulse width, pulse repetition frequency, for an electrical stimulation signal);

one or more parameters that affect operation of an algorithm or method executed by device 102 (e.g. an amount to increment a stimulation level when it is desired to increase blood pressure, an amount to decrement a stimulation level when it is desired to decrease blood pressure, a lag time to wait before further adjusting the stimulation level etc.).

The appropriate stimulation output may, for example, be based on a predetermined target blood pressure range for an individual. The target blood pressure range may, for example, be predetermined by a medical professional (e.g. a physician, pharmacist, physician-aid or other trained operator). The target blood pressure range may be predetermined based on the resting blood pressure of the subject prior to stimulation, and/or other criteria as determined by a medical professional. In some embodiments the target blood pressure range is adjustable based upon a user input that allows a medical professional and/or the subject to move the target blood pressure range toward higher or lower blood pressures. The user input may be provided for example using programmer 102G or some other interface that is connected to control device 102.

The appropriate stimulation output may also be based on the comfort and/or safety of the subject. For example, the stimulation output may be selected so that a stimulation level is kept lower than a threshold above which the stimulation becomes uncomfortable to the subject and/or causes side effects such as spasticity.

The appropriate stimulation output may optionally based on a mode of operation of device 102. For example, device 102 may have a plurality of routines where each routine may specify different parameters. For example, a "Morning sit up stimulation routine" may control for a higher blood pressure than an "afternoon resting routine". In some embodiments a subject may select among the plurality of routines using programmer 102G or some other interface that is connected to control device 102. In some embodiments, device 102 incorporates a scheduler that automatically selects one of a plurality of routines based on time of day.

The appropriate stimulation output may be expressed as characteristics of one or more electrical stimulation signals to be delivered to the subject. These characteristics may, for example, comprise:

an amplitude (e.g. voltage and/or current) of the signal(s),
an electrical pulse frequency of the signal(s),
a pulse width of stimulation,
a polarity of the stimulation,
a selection of electrodes for delivery of the stimulation,
other electrical characteristics of the signal(s); or
any combination/permutation of these factors.

Figure 2:
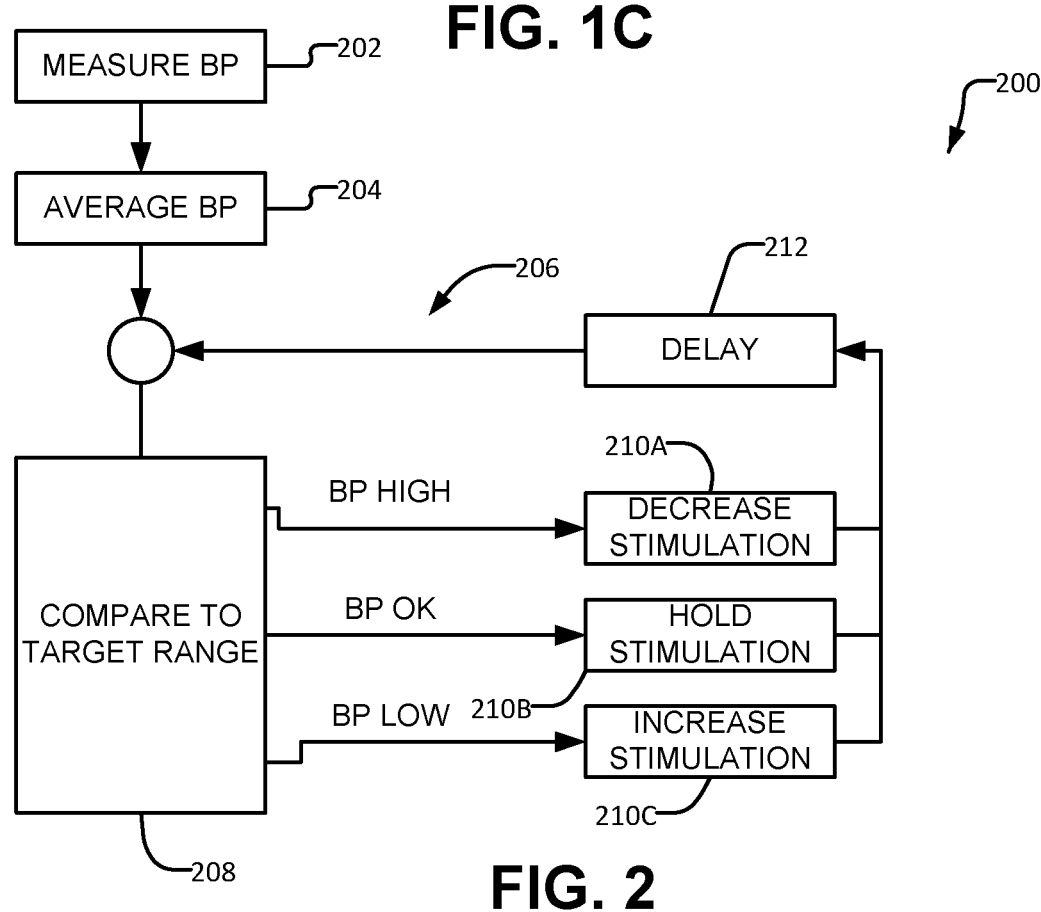
FIG. 2 is a flow chart showing an example method for operating apparatus to control an autonomic function of a subject such as the subject's blood pressure.

FIG. 2 illustrates an example feedback control/decision making algorithm 200 that may be used in accordance with the present invention. Such an algorithm may, for example, be implemented using software instructions 102E. Block 202 receives a stream of blood pressure measurements. For example, blood pressure measurements may be received on the order of a few to a few tens of measurements per minute. Block 204 determines a running average blood pressure that is made available to the rest of method 200. Block 204 may, for example, determine an average blood pressure for an immediately previous period. For example, the average may be determined for a period having a length of a few seconds to a few minutes (e.g. 30 seconds).

Method 200 includes loop 206 which begins by comparing the current average blood pressure from block 204 to the target range. If the presently measured average blood pressure exceeds the target range then block 201A triggers a reduction of the stimulation level. If the presently measured average blood pressure is within the target range then block 210B holds the stimulation at the current level. If the presently measured average blood pressure is below the target range then block 210C triggers an increase of the stimulation level. Block 212 delays for a short period before the next iteration of loop 206.

An increase or reduction of the stimulation level may be achieved by incrementally increasing or reducing the stimulation level. The increments may be predetermined fixed increments or may be set based on factors such as how far away from the target range is the presently measured blood pressure. In an example embodiment the increment size is increased in proportion to a difference between the presently measured blood pressure and the closest part of the target blood pressure range. Increments for increasing and decreasing the stimulation level may be the same or different. Another way to increase or reduce the stimulation level comprises ramping the stimulation level up or down. The rate(s) at which the stimulation level are ramped up or down may be fixed or variable. In some embodiments the rates of increase and/or decrease are set as a function of a difference between the presently measured blood pressure and the closest part of the target blood pressure range. The rates of increase and/or decrease may be higher when a difference between the presently measured blood pressure and the closest part of the target blood pressure range is larger.

Figure 2A:
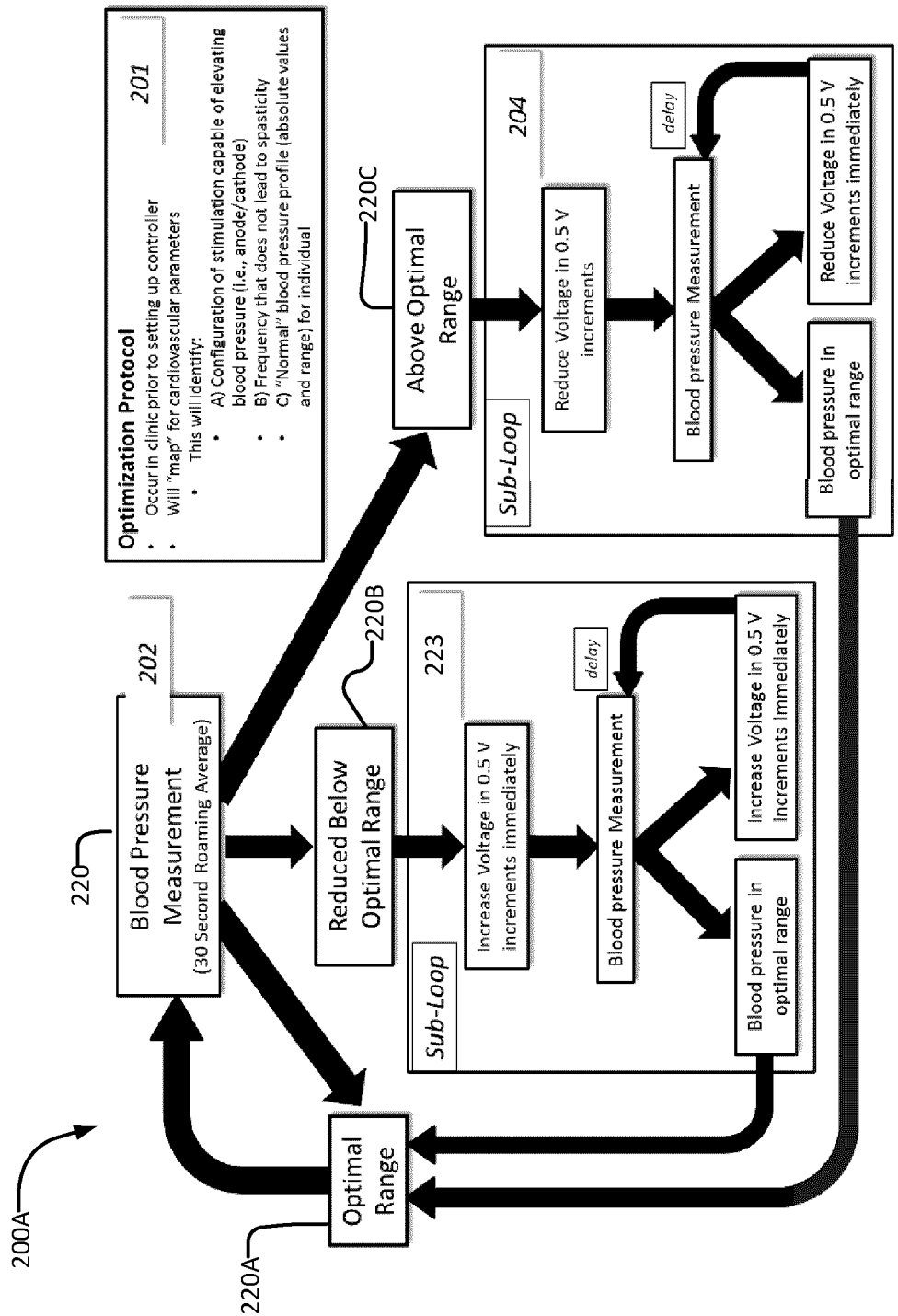
FIG. 2A is a flow chart illustrating another example control mechanism with feedback loops to be engaged when blood pressure is either above or below a predetermined target range.
Figure 3A:
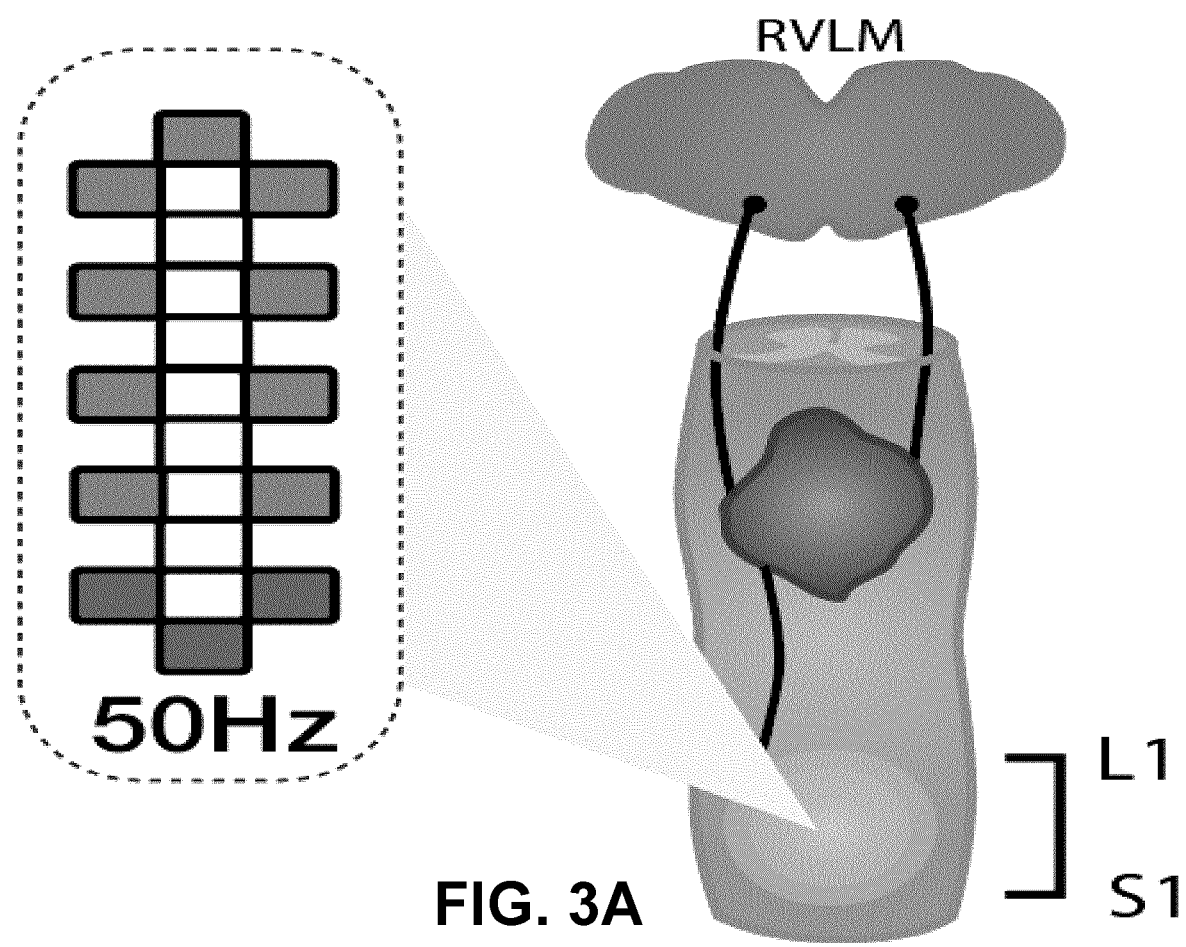
FIGS. 3A to 3G illustrate the restoration of cardiovascular control in individuals with SCI in response to controlled electrical spinal cord stimulation.
Figure 3B:
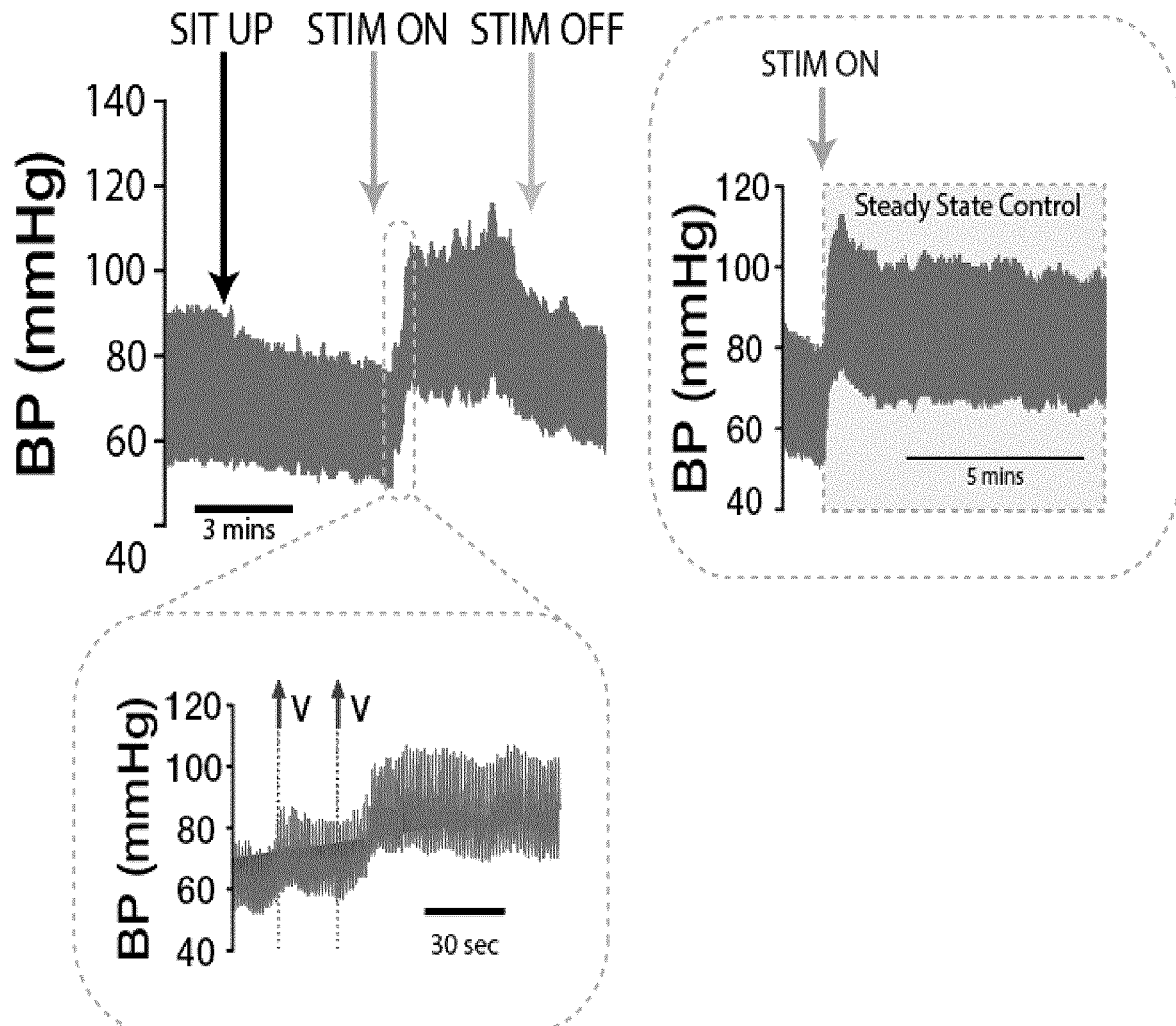
Figure 3C:
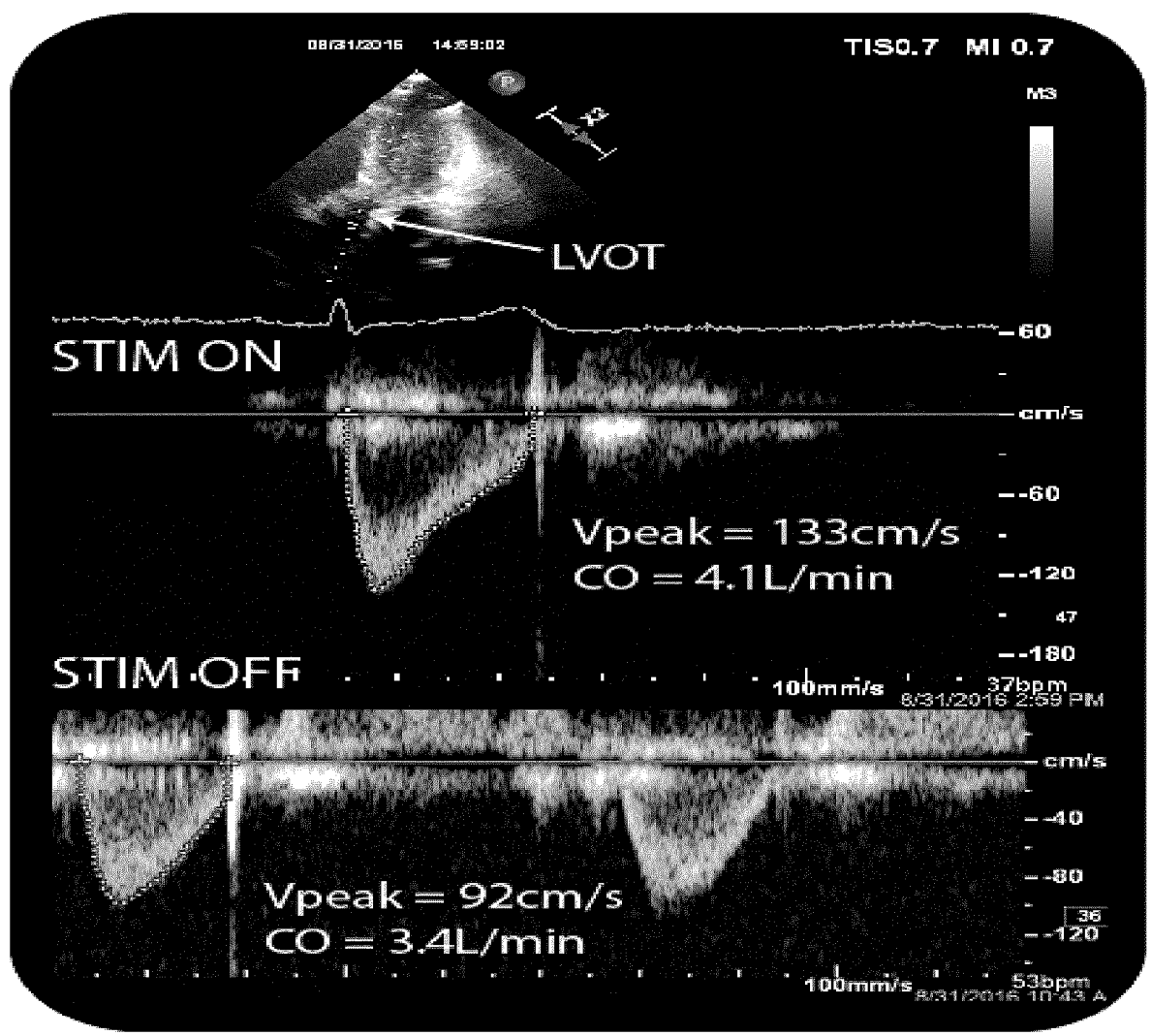
Figure 3D:
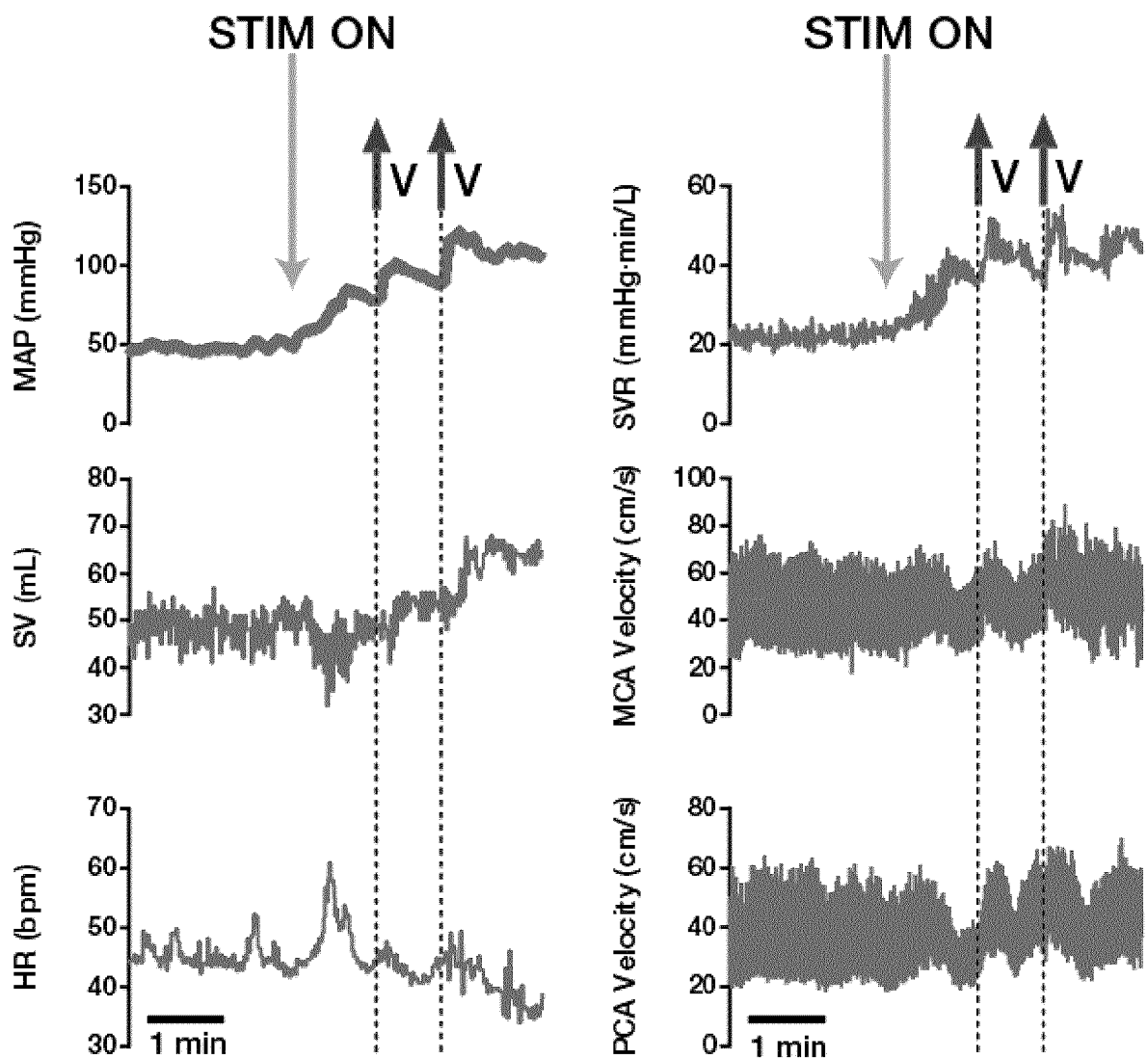
Figure 3E:
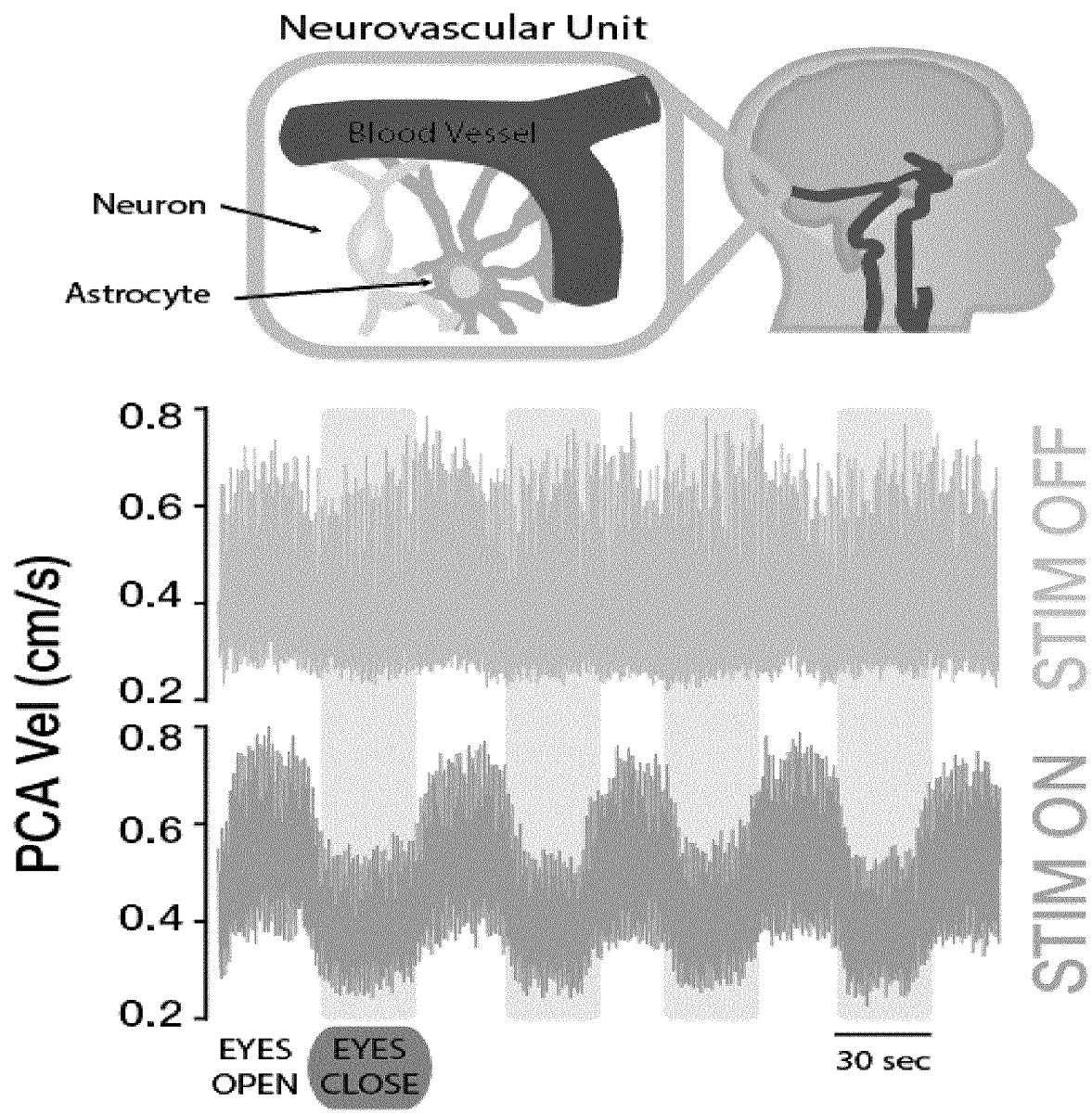
Figure 3F:
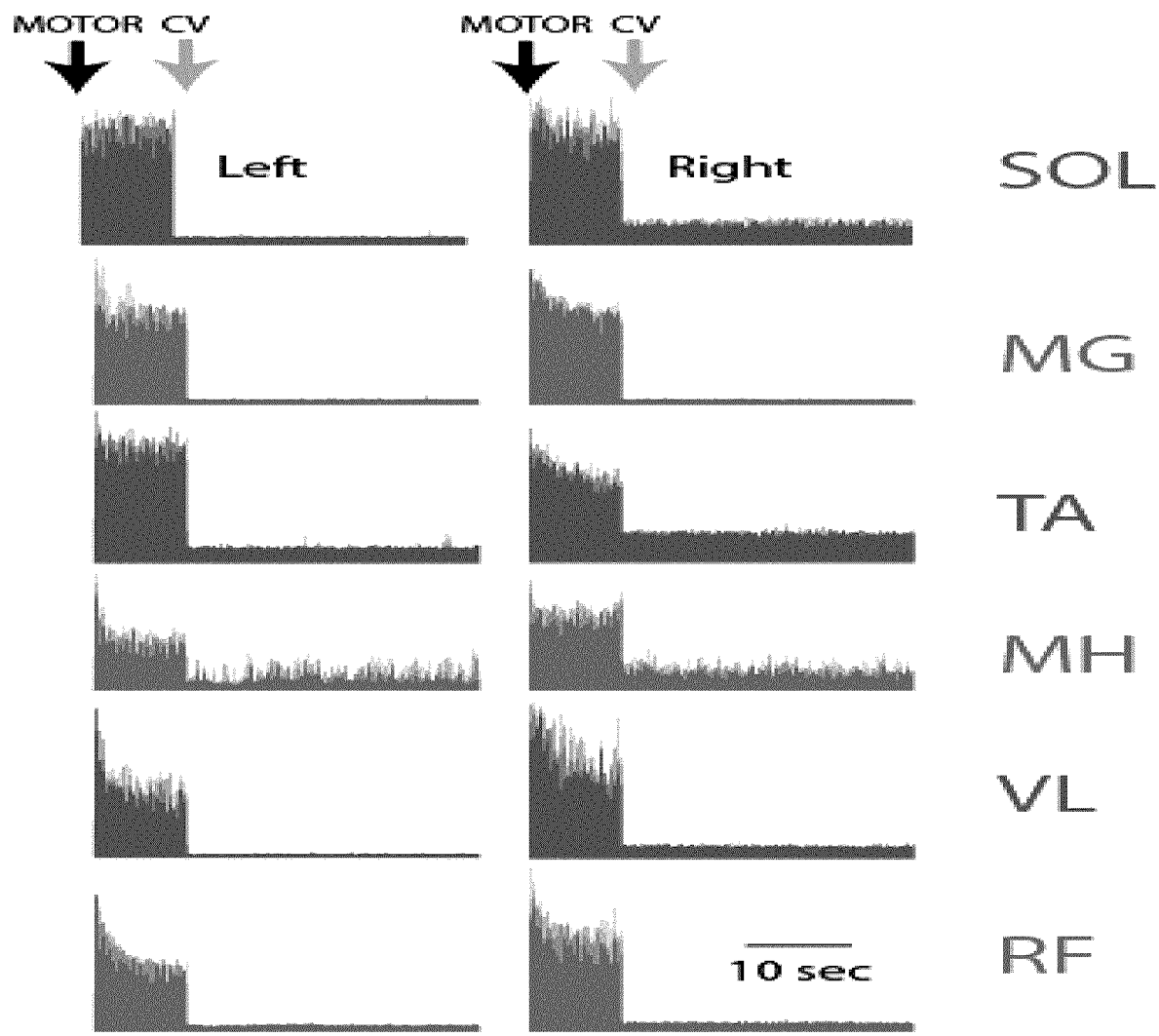
Figure 3G:
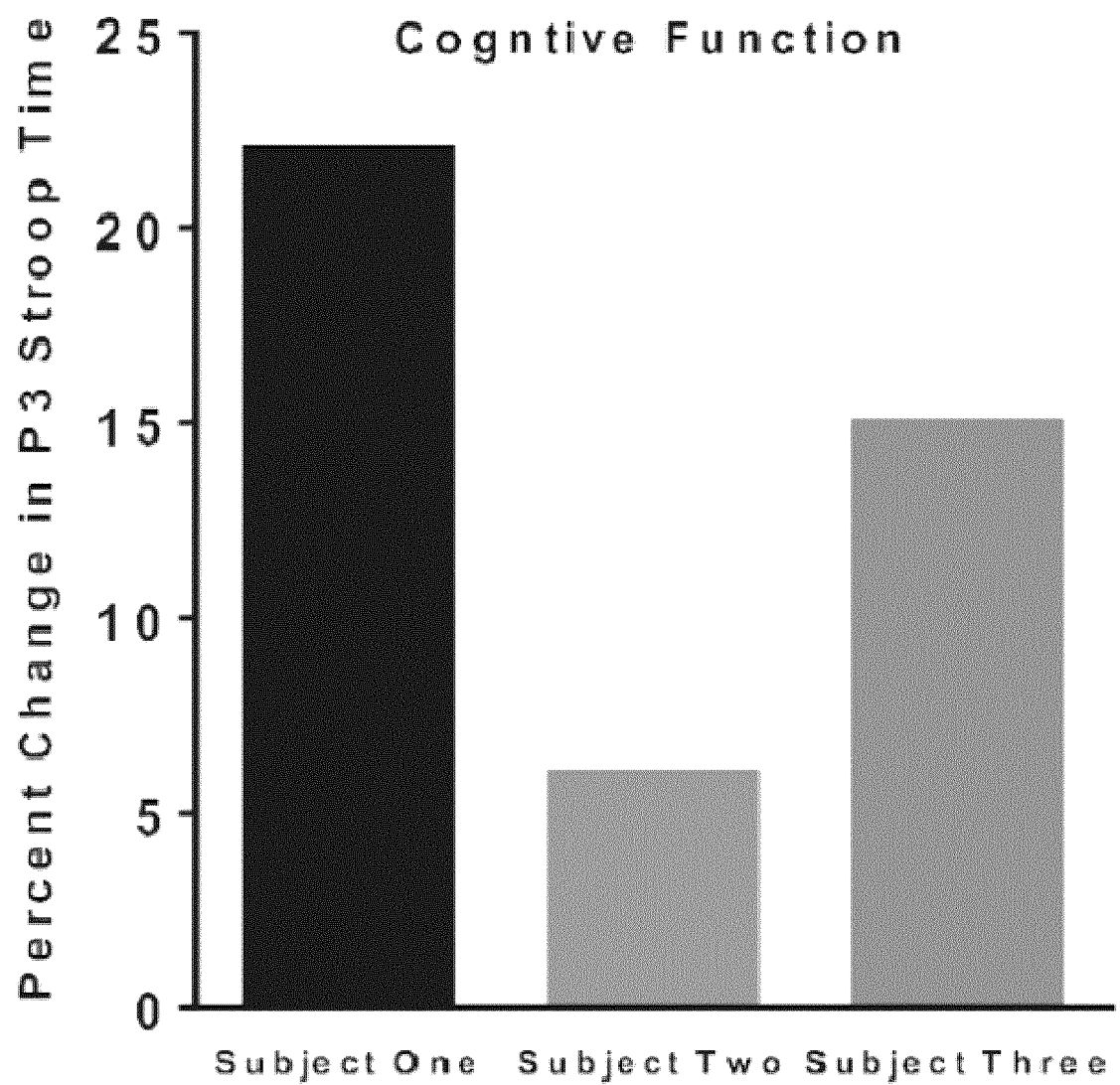

FIG. 2A shows another example of a blood pressure feedback control algorithm 200A that may be executed by a device 102 and/or a feedback circuit 14. Control algorithm 200A may detect whether the measured blood pressure of a subject (220) is within the target range (block 220A) or outside of the target range. If the measured blood pressure of a subject is below the predetermined target range (block 220B) then sub-loop 223 is engaged. In sub-loop 223 the stimulation level supplied by stimulation apparatus 103 is elevated. This may be done, for example, by increasing a voltage and/or current of an electrical stimulation signal and/or by adjusting a frequency of the electrical stimulation signal to a frequency that is more effective for increasing blood pressure. For example, the stimulation voltage or current may be increased incrementally by performing sub-loop 223 until the target blood pressure range is reached.

In some embodiments the stimulation voltage is elevated in increments having sizes in the range of 0.1 V-10 V. The stimulation assembly may be configured, for example, to elevate voltage in 0.5 V increments. The voltage may be elevated incrementally. The voltage increments may be predetermined by a medical professional. The voltage increments may be determined on a per subject basis.

The increments may be selected depending on the type of stimulation assembly used. For example, where an epidural stimulation assembly is used, the electrical stimulation may be elevated in increments in the range of about 0.1V to 30 V (preferably about 0.4V to about 2.5V). As another example, where a transdermal stimulation assembly is used, the electrical stimulation may be increased by delivering higher currents. For example, electrical current may be elevated in increments in the range of about 0.1 to about 150 mA (preferably the increments of electrical current are about 20 mA).

If blood pressure does not elevate into the target range in response to an incremental increase in stimulation level, then sub-loop 223 may further increase stimulation voltage at the predetermined increment until a blood pressure within the target blood pressure range is reached or until a maximum stimulation level has been reached. As mentioned above, the maximum stimulation level may be set to preserve the subject's comfort and/or safety.

In some embodiments method 200 stops increases in stimulation level in response to receiving a "STOP" command. The stop command may be issued in response to the subject activating a button or other control, for example.

Blood pressure may not respond instantaneously to excitation of sympathetic preganglionic neurons, and therefore there may be a lag between commanding a change in a stimulation level and a consequential change in the subject's blood pressure. For this reason, method 200 provides a lag duration between a time when a stimulation level is set and a next time at which the stimulation level adjustment. This lag may be on the order of seconds, for example. In some embodiments the lag is at least 10 seconds. The device can operate with a variety of lag durations from 1 second to an hour or more on a per subject basis. Preferably, the device provides a lag duration in the range of a few seconds to 15 minutes. More preferably, the device provides a lag duration of about 10 seconds.

In some embodiments the lag is variable. For example, the lag may be reduced in cases where the presently measured blood pressure is far from the target range and the lag may be increased in cases where the presently measured blood pressure is close to or within the target range.

If a blood pressure within the target range is reached (block 220A), the stimulation level may be maintained until blood pressure deviates from the target range.

If blood pressure is above the upper threshold of the predetermined target range (block 220C) then sub-loop 224 is performed to reduce blood pressure by reducing the stimulation level supplied by stimulation system 103. For example, stimulation voltage and/or current may be reduced. In this manner the stimulation level may be reduced until a blood pressure within the target blood pressure range is reached.

The reduction may be incremental. For example, voltage and/or current increments may be predetermined by a medical professional and may be the same as or different from the increment used in sub loop 223. The increments may be determined on a per subject basis. Stimulation voltage may be reduced in increments in the range of 0.1 V-10 V for example. Preferably, stimulation assembly 103 reduces voltage in increments of about 0.5 V each time sub-loop 224 is executed. If a blood pressure within the target range is reached (block 220A), the stimulation intensity may be maintained until blood pressure deviates from the target range.

The stimulation increments may vary depending on the type of stimulation assembly used. For example, where a transdermal stimulation assembly is used, the electrical stimulation may be decreased in increments in the range of about 0.1 mA to about 150 mA (preferably about 20 mA). Where an epidural stimulation assembly is used, the electrical stimulation may be decreased in increments in the range of about 0.1V to about 30V (preferably about 0.3V to 2.4V, for example 2V, more preferably about 0.5V).

If blood pressure does not decrease sufficiently in response to an incremental decrease in voltage by sub-loop 224, then stimulation voltage may be further decreased by the predetermined increment until a blood pressure within the target blood pressure range is reached.

Blood pressure may not respond instantaneously to the reduction of excitation of sympathetic preganglionic neurons, and therefore there may be a lag of at least 10 seconds between stimulation and the subsequent blood pressure detection and voltage adjustment. The device can operate with a variety of lag durations from 1 second to several hours on a per subject basis. Preferably, the device can operate with a lag duration from a few seconds to 15 minutes. More preferably, the device operates with a lag duration of less than about 1 minute, such as a lag duration of about 10 seconds.

In some embodiments, the stimulation output has one or any combination of two or more of the following characteristics:

the stimulation output comprises electrical pulses presented at a pulse frequency in the range of about 5 Hz to 10 kHz (preferably about 30 Hz to about 60 Hz).

the stimulation output comprises electrical pulses having a pulse width in the range of about 0.002 seconds to about 20 seconds (preferably about 0.033 seconds to about 0.17 seconds).

the stimulation output has a voltage in the range of about 0.1 V to about 24 V.

the stimulation output has a voltage in the range of about 0.1 V to about 500 V.

the stimulation output has an amperage in the range of about 0 mA to about 1000 mA.

In preferred embodiments where the stimulation signals are delivered by way of an epidural stimulator the stimulation output has a voltage in the range of about 0.1 V to about 20 V and an amperage in the range of about 0 mA to about 100 mA.

In preferred embodiments where the stimulation signals are delivered by way of a transcutaneous stimulator the stimulation output has a voltage in the range of about 0.1 V to about 100 V and an amperage in the range of about 0 mA to about 100 mA.

In accordance with one aspect of the invention, the device may be used to control blood pressure in a subject with dysregulated blood pressure. The dysregulated blood pressure may be due to SCI or other neurological conditions including, but not limited to, multiple sclerosis, autonomic failure, autonomic neuropathy, as well as cancer of the neurological tissue. The device may be used to control blood pressure in a subject with SCI. In one aspect of the invention, the device may control electrical stimulation of the spinal cord. Electrical stimulation of the spinal cord may be performed caudal to injury. Electrical stimulation of the spinal cord may be performed at spinal segments T1-L1, as well as anywhere over the thoracic segment where sympathetic preganglionic neurons are stimulated to elicit a blood pressure effect.

Methods and apparatus as described herein may be applied in combination with pharmacological agents that affect blood pressure. For example, methods and apparatus as described herein may be applied to a subject who is being treated with a pharmacological agent for increasing blood pressure. The use of the present apparatus and methods may reduce the dosage of the pharmacological agent required and/or the time between doses of the pharmacological agent. This may reduce side effects of the pharmacological agent in some cases. Further, use of the present apparatus and methods may advantageously maintain control over blood pressure during the time required for a dose of the pharmacological agent to take effect.

The present invention may be applied to control autonomic functions other than blood pressure. For example, apparatus and control algorithms as described herein may be applied for controlling a variety of autonomic processes in a subject using electrical or other stimulation. Autonomic processes may include regulation of blood pressure, bladder/bowel control, sexual function, etc.

A device comprising a circuit 14 as described herein may receive input from any of a variety of physiological monitors and control a variety of electrical stimulation assemblies in response to the inputs. Such a device may be configured to receive information from the physiological monitor, and analyze such information based on a control algorithm as described above for example. The device may be configured to direct the electrical stimulation assembly to transmit output electrical stimulation based on the control algorithm. The output electrical stimulation may be transdermal or epidural. Epidural delivery of electrical stimulation is preferred. The stimulation output may increase or decrease depending on the information received from the physiological monitor. The stimulation output may remain constant depending on the information received from the physiological monitor. The stimulation output may improve control of any of a range of autonomic functions. The control interface may operate by feedback control.

For example, epidural spinal cord stimulation as described may be applied to acutely modulate bladder and/or bowel function in subjects affected by SCI. This may be done by providing a program to deliver stimulation that facilitates urination and/or bowel function and providing an interface that allows a subject to input a command to perform the program. The program may specify a type of stimulation that is specific to bladder/bowel control and that does not significantly affect blood pressure or other functions. A device as described herein may be configured to temporarily suspend active control over BP while performing a bowel/bladder control program and/or the bladder/bowel control program may be performed in parallel with control of blood pressure or other autonomous functions as described herein.

For example, in an example case a program that involved applying electrical stimulation comprising a pulse width 450 ms, a frequency of 45 Hz, and an intensity of 6V for a stimulation time of 105 s led to an increase in external anal sphincter/pelvic floor muscle tone (as measured by EMG) and detrusor pressure (Pdet). This stimulation was found to reduce the time required for bowel evacuation from 117 to 23 minutes (i.e. >80%). The stimulation was applied using a subset of the electrodes provided by an implanted 16-electrode array (Specify 5-6-5, Medtronic, Minneapolis, Minn., USA) placed at the T11-L1 vertebral levels and driven by a neurostimulator (RestoreAdvanced SureScan™ MRI neurostimulator). The subset of electrodes was selected to affect bladder/bowel function.

Figure 8A:
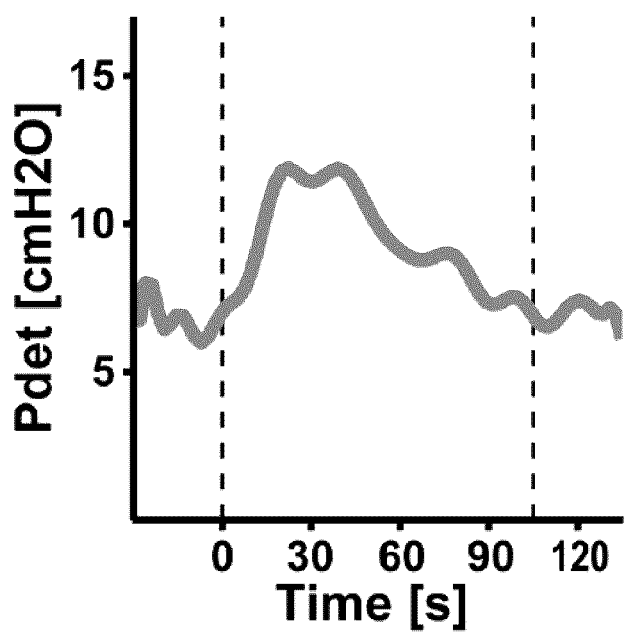
FIGS. 8A, 8B and 8C are graphs respectively illustrating the effect of stimulation to control bladder/bowel function on detrusor pressure (Pdet), floor muscle tone (EMG) and blood pressure (BP)/heart rate (HR)
Figure 8B:
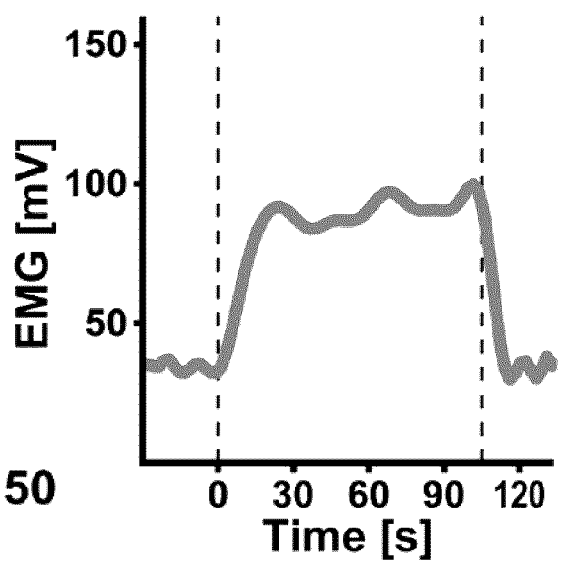
Figure 8C:
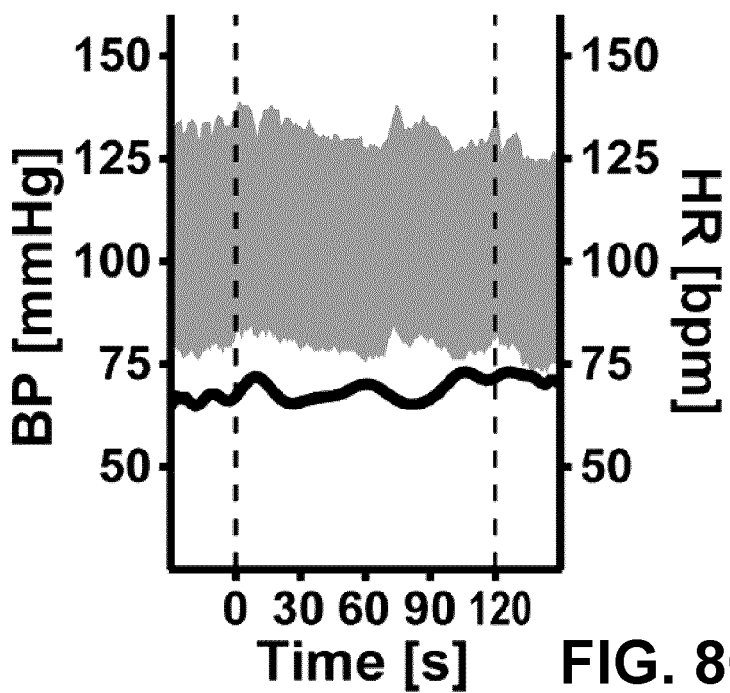

FIGS. 8A to 8C show that the stimulation led to an increase in external anal sphincter/pelvic floor muscle tone (EMG) and detrusor pressure (Pdet). Blood pressure (BP) and heart rate (HR) remained stable during stimulation. Dashed lines indicate start and stop of stimulation.

In some embodiments blood pressure monitor 101 is replaced with a monitor for measuring urinary bladder/bowel volume. In such embodiments a measured bladder volume may be processed to alter signals delivered to control bowel/bladder function.

Without committing to any particular theory of operation, it is thought that stimulation delivered by way of such electrodes may activate sympathetic and/or parasympathetic spinal neuronal structures in the lower part of the spinal cord to cause changes of functions in blood vessels, bladder, bowel and/or sexual organs. The neuronal structures involved may be located within the T11 to S5 segments of the spinal cord, for example. Stimulation may be configured to control a particular function by selecting electrodes and/or the nature of the stimulation.

The desired structures may be stimulated transdermally. Transdermal stimulation may incidentally also activate afferent fibres in skin/underlying tissue.

Blood pressure or another function may be controlled by electronic feedback control. This may be done by monitoring one or more parameters that indicate activity of the function being controlled and setting a level of the stimulation based on the monitored parameters. In the case of blood pressure the monitored function may be blood pressure itself (measured using any available blood pressure monitoring modality). The stimulation level may be controlled to keep blood pressure within a target range. Such stimulation may be particularly useful for raising blood pressure to counteract the extreme hypotension that often accompanies SCI.

In some embodiments the method involves administering to the subject pharmacological agents that have the effect of raising blood pressure and adjusting the stimulation level automatically to maintain the desired blood pressure taking into account the effect of the pharmacological agent. This control may cause the stimulation level to be higher in the period before the pharmacological agent takes full effect. The stimulation level may be lower (or off) when the pharmacological agent is fully effective. The stimulation level may then increase as the pharmacological agent is metabolized or excreted or otherwise ceases to maintain blood pressure.

In some embodiments the method may comprise selection of a program for control of an autonomic function. Different programs may be provided for the same autonomic function. Different programs may differ, for example, in one or more of:

Target level for the function (e.g. target blood pressure range);
Lag time for control (e.g. time constant for feedback);
Rate of increase or decrease of stimulation level;
Maximum allowed stimulation level
etc.

A program may be selected from among a plurality of programs in response to user input by way of a suitable control, an automatic scheduler and/or the like. Where the stimulation is delivered by way of apparatus as described herein, programs may be defined by stored data which may be resident in a control circuit (e.g. 102) or a stimulator (e.g. 103) or a device which combines these functions, for example.

In some embodiments the method may include control of plural autonomic functions. For example, the method may involve controlling blood pressure and also controlling bladder/bowel function. In such cases, different stimulation may be provided for each of the autonomic functions. The stimulation for the different functions may be selected in such a manner that the stimulation associated with one function does not significantly affect another function. This may be achieved, for example, in the case of electrical stimulation, by one or more of:

using different combinations of electrodes for stimulation of the different functions;
using different polarities of stimulation;
using different frequencies, waveforms or other stimulation signal characteristics for the different functions etc.

Control of the bladder/bowel function may be applied selectively to assist a subject with urination and/or bowel voiding. Where this is done in combination with control over blood pressure the stimulation for blood pressure control may be performed concurrently with stimulation of bowel/bladder function or the stimulation for blood pressure control may be temporarily interrupted while applying stimulation for bowel/bladder function.

Stimulation for sexual function may be handled in the same or a similar way to stimulation for bowel/bladder function.

EXAMPLES

Prototype embodiments of systems as described herein have been tested on a number of subjects in a study that was approved by the clinical research ethics board of the University of Louisville, the University of California Los Angeles, and the University of British Columbia. Each of the subjects presented with motor, sensory, and autonomic completeness of injury. Each of the subjects provided written informed consent. All subjects of the study were:
  screened for the presence of orthostatic intolerance and exhibited a reduction in systolic arterial blood pressure of at least 20 mmHg in response to a sit-up test.
  assessed for neurological level and completeness of injury according to standard guidelines.

Epidural Electrical Spinal Stimulation

An epidural spinal cord stimulation unit (RestoreAD-VANCED™, Medtronic, Minneapolis, Minn., USA) in combination with a 16-electrode array paddle 301 (see FIGS. 3A to 3G). Paddle 301 was a 5-6-5 paddle from, Medtronic, Minneapolis, Minn., USA. Paddle 301 was implanted at T11-L1 vertebral levels over the lumbosacral spinal cord segments.1 During the implantation surgery, the electrode array was positioned over the midline of the exposed dura and its location was assessed intraoperatively with thresholds and amplitudes of electromyography (EMG) recorded from leg muscles elicited by stimulation at 2 Hz. Two wide-field stimulation configurations, where the anodes where located at the most rostral three locations on the electrode, and the cathodes were located at the most caudal three portions of the electrode, (or vice versa) were used for stimulating and eliciting these effects.

General Integrated Hemodynamic Assessment Approach

At least one month after implantation surgery, and following the development of a cardiovascular optimized stimulation paradigm (CV-scES); i.e., elucidating the optimum stimulation parameters that could modulate blood pressure), we conducted a within person trial to investigate the immediate cardiovascular effects of CV-scES. The three participants were randomized to receive either stim-on or stim-off condition first and the two testing sessions were separated by no more than 24 hours.

FIG. 3 includes beat-by-beat blood pressure via finger photoplethysmography (Finometer PRO™, Finapres Medicine Systems, Amsterdam, Netherlands) corrected to brachial pressure (Dinamap, General Electric Pro 300V2; Tampa, Fla., USA), electrocardiogram, central sympathetic outflow via sympathetic skin responses, cardiac function via echocardiography (Phillips EPIQ7™, Philips Medical System, Andover, Mass., USA), and neurovascular coupling by insonating the middle and posterior cerebral arteries with a transcranial Doppler (ST3 Transcranial Doppler™, Spencer Technologies, Redmond, Wash., USA). During the sit-up position only, we also assessed executive function (i.e., verbal fluency), as well as attention/concentration (Stroop test; FIG. 3 Part 306). All procedures were assessed in the supine position and then in response to sit-up with and without stimulation.

Example 1: Restoration of Integrated Cardiovascular Control in Response to Epidural Stimulation FIG. 3. illustrates the cardiovascular response of an individual following controlled electrical stimulation. All panels show raw cardiovascular data for one study participant. Parts 304 and 302 show the participant's acute blood pressure responses to increases and decreases in voltage where blood pressure is accurately controlled and regulated by titration of stimulation up and down, and subsequent increases in voltage lead to further increase in blood pressure. Part 302 shows that acute reductions in voltage can reduce blood pressure in a controlled and incremental way.

Raw blood pressure traces 302 indicate that when the stimulator was activated there was an immediate reversal of orthostatic hypotension that was achieved in a controlled manner by gradually increasing voltage. Orthostatic hypotension prevailed again when the stimulator was turned off, demonstrating a capability to dynamically modulate blood pressure. Under steady state conditions, the stimulator was able to offset chronic hypotension by increasing and maintaining blood pressure approximately 20 mmHg above resting baseline, and increased low-frequency oscillations in systolic blood pressure indicating a return of medullary cardiovascular control.

Raw echocardiography imaging 303 of the left-ventricular outflow tract in the seated position demonstrates that peak outflow velocity and cardiac output are increased with stimulation.

Model-flow estimations 304 of mean arterial blood pressure, stroke volume, heart rate and systemic vascular resistance obtained from finger plethysmography along with raw transcranial Doppler images of the mid cerebral artery (MCA) and the posterior cerebral artery (PCA). Note the stepwise increase in all variables when the stimulator was activated (V), except heart rate which was offset due to the associated increase in stroke volume.

Raw changes in PCA velocity in response to cerebral activation (eyes open) 305 indicate the complete restoration of neurovascular coupling with stimulation (i.e., appropriate regulation of PCA velocity with cerebral activation). Lower-limb electromyography responses 305 to both low-frequency 'motor-optimized' and high-frequency 'cardiovascular-optimized' epidural stimulation reveal no concurrent motor activity during CV-optimized stimulation.

Figure 4:
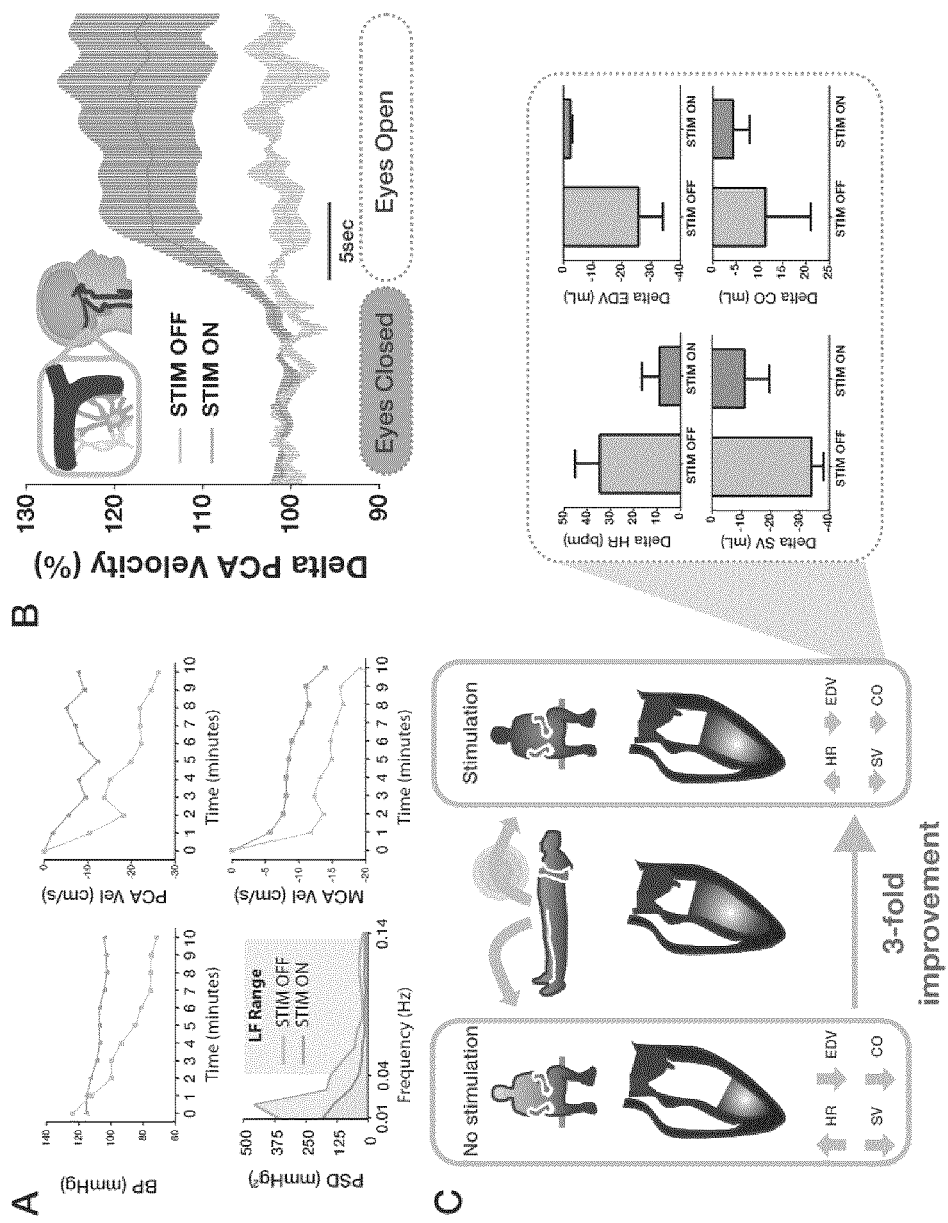
FIGS. 4 and 4A to 4C illustrate improved cardiovascular function in individuals with SCI that received optimized epidural spinal stimulation.
Figure 4A:
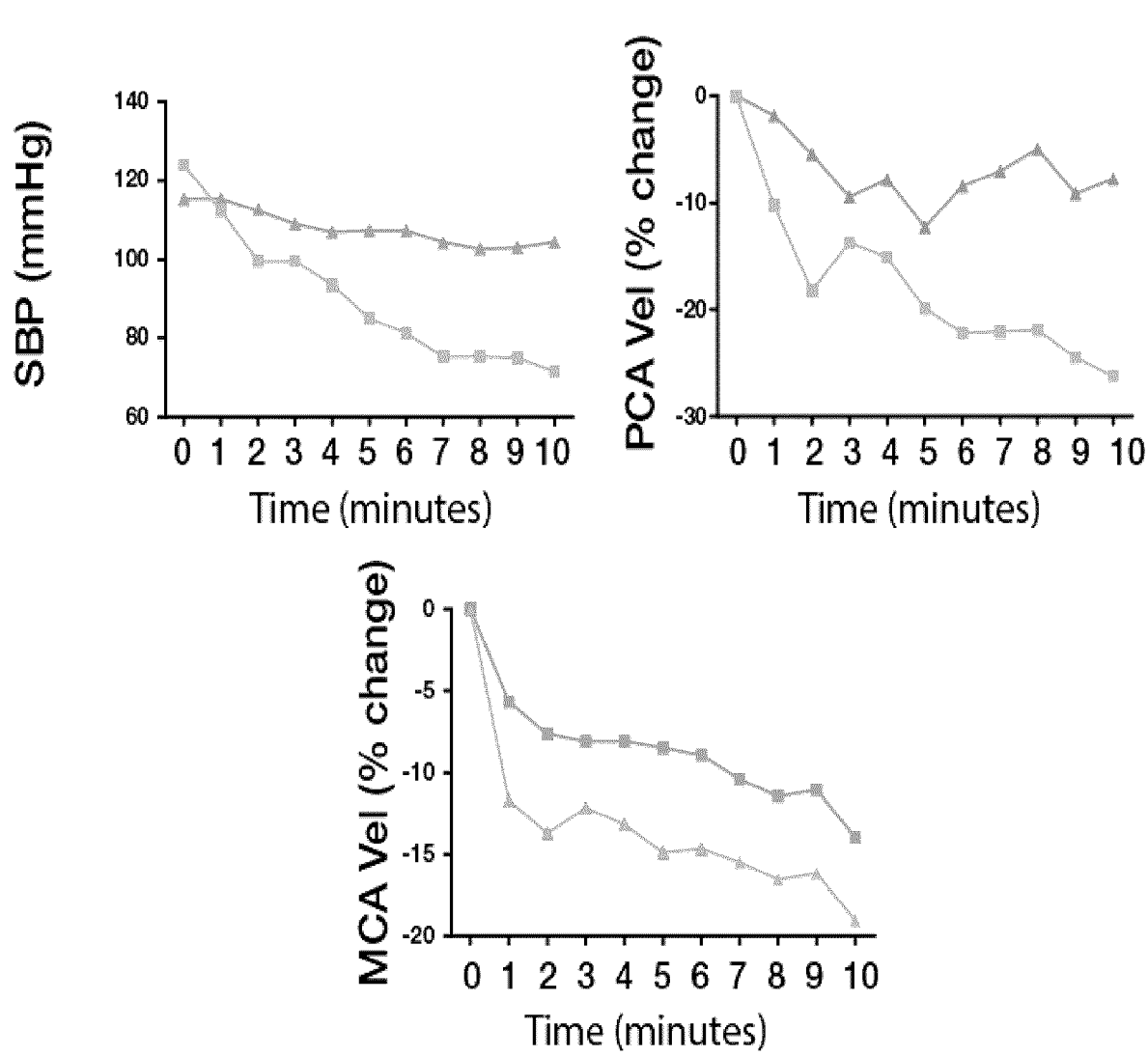
Figure 4B:
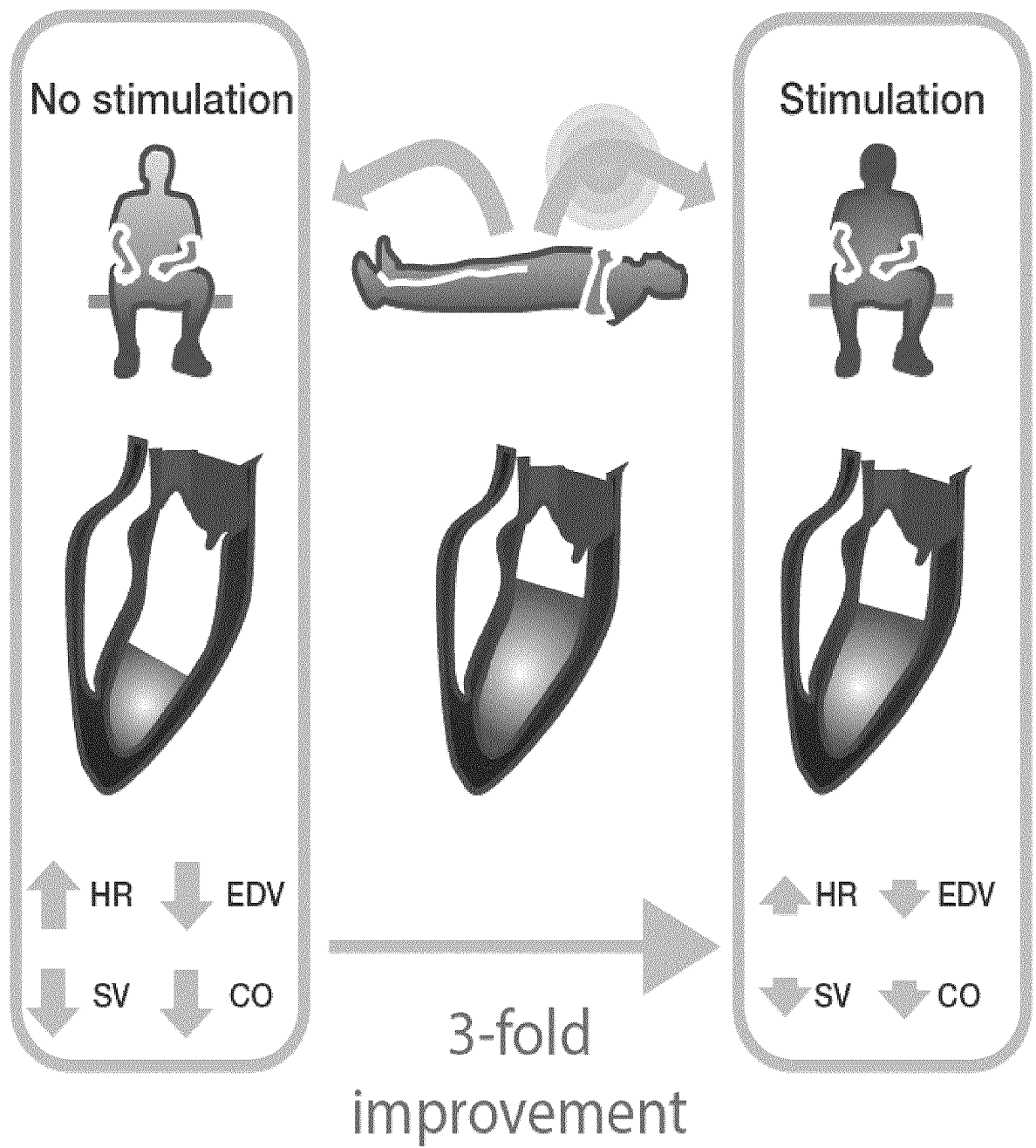
Figure 4C:
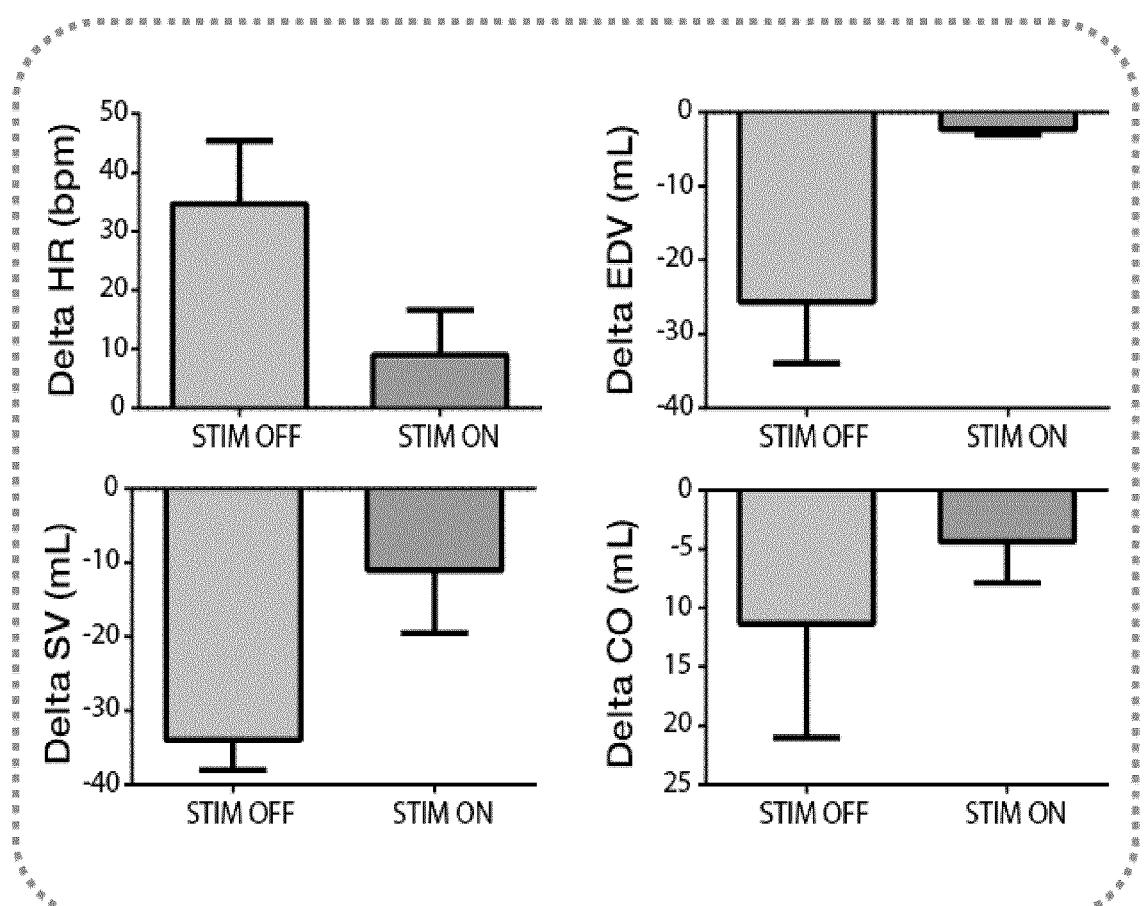
Figure 5A:
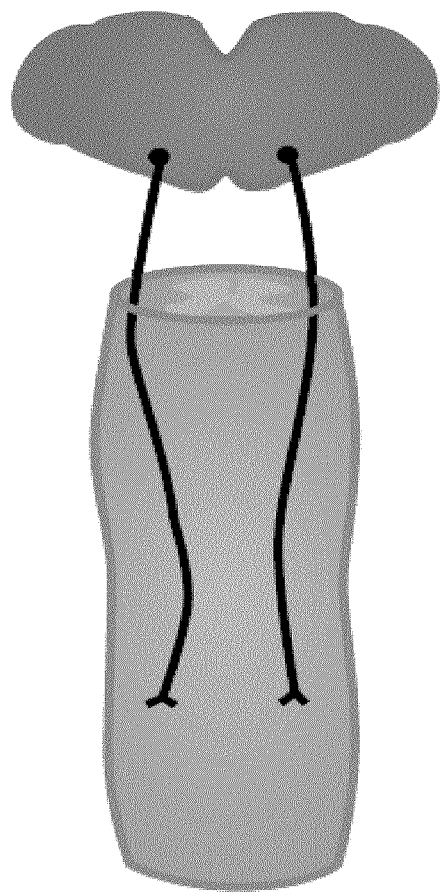
FIGS. 5A to 5C demonstrate how potentiation of sympathetic circuitry may restore dormant sympathetic cardiovascular pathways.
Figure 5A:
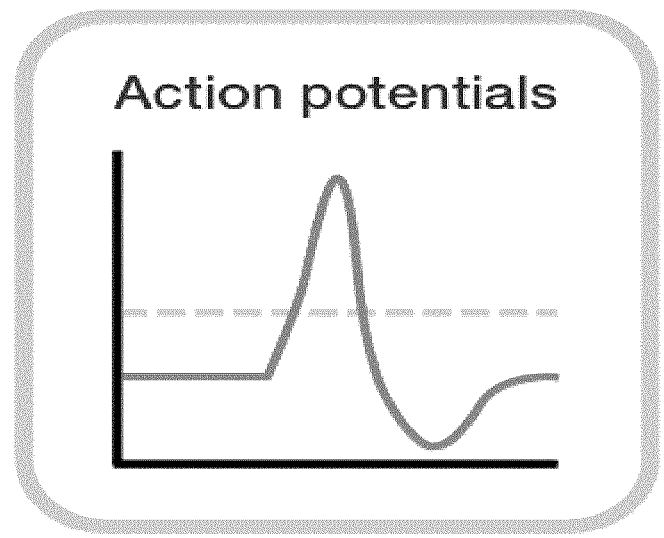
Figure 5A:
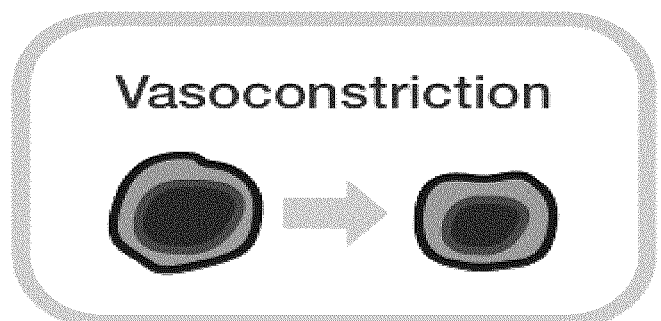
Figure 5B:
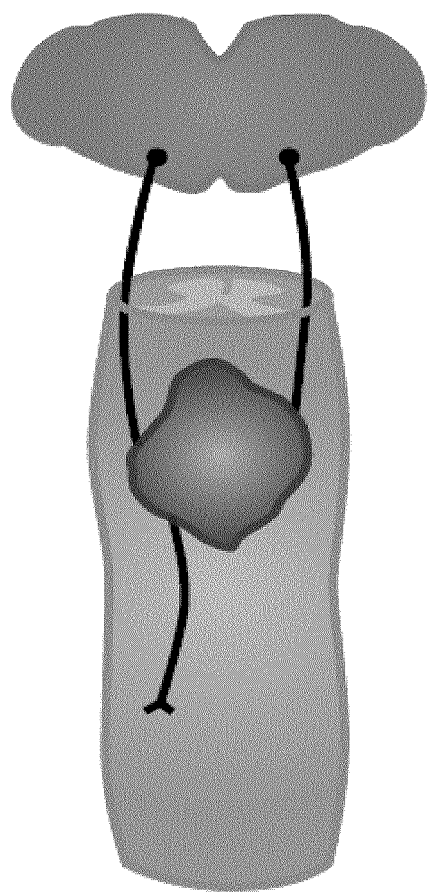
Figure 5B:
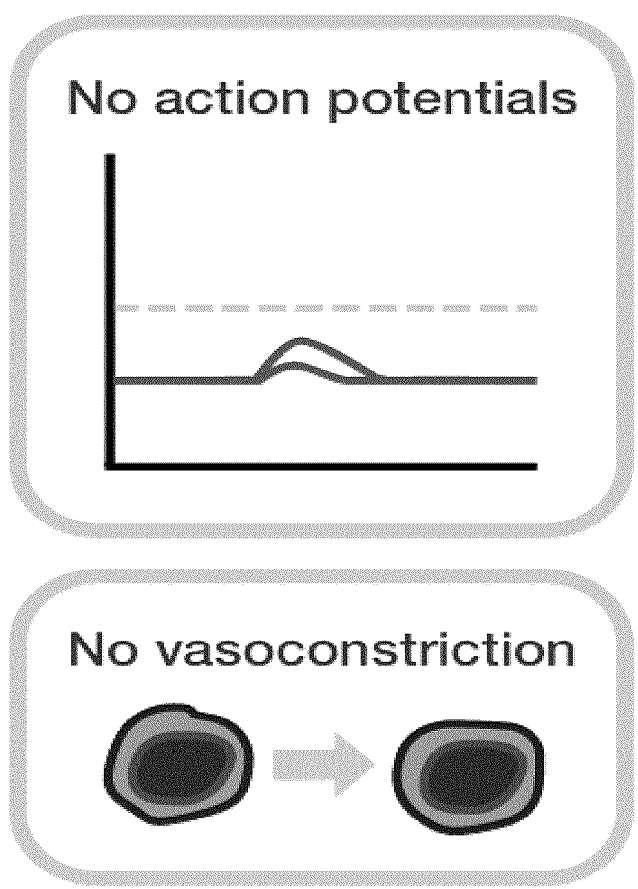
Figure 5C:
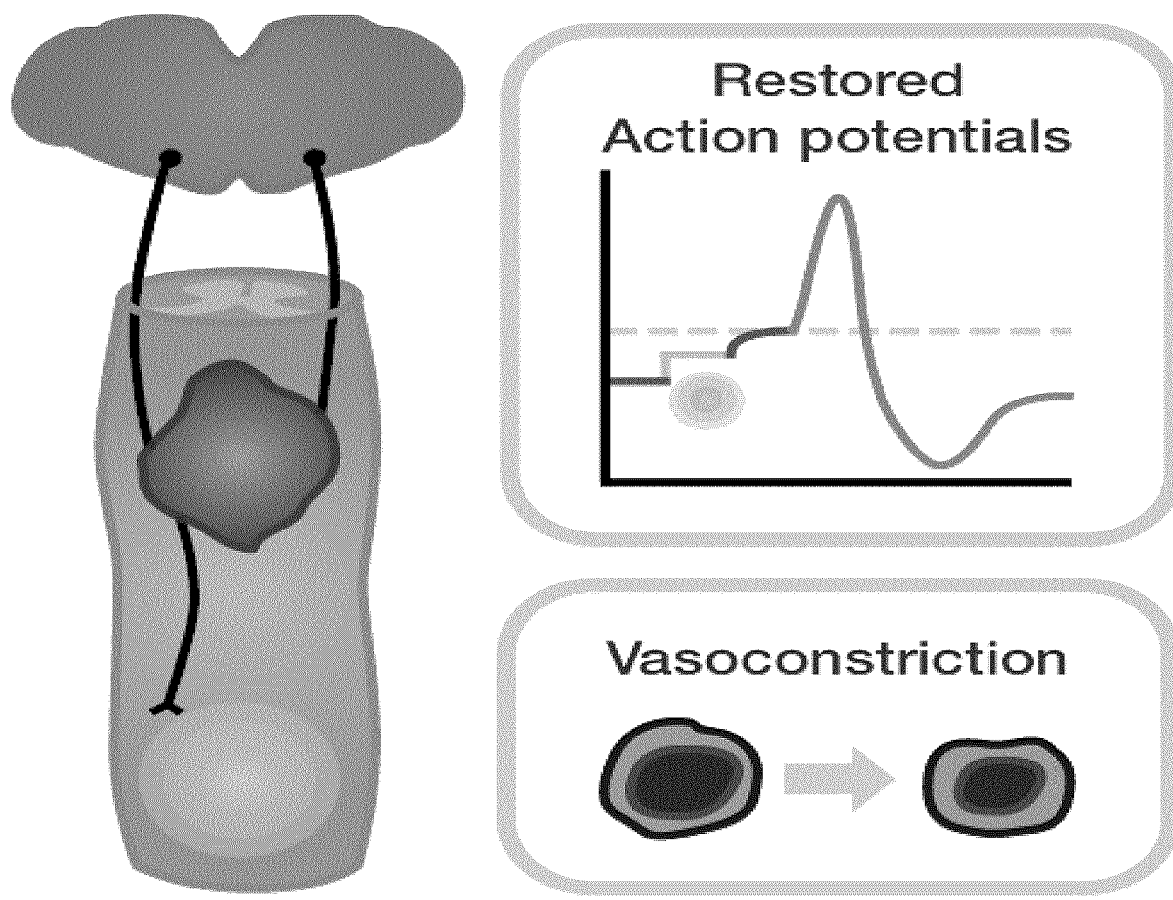
Figure 7:
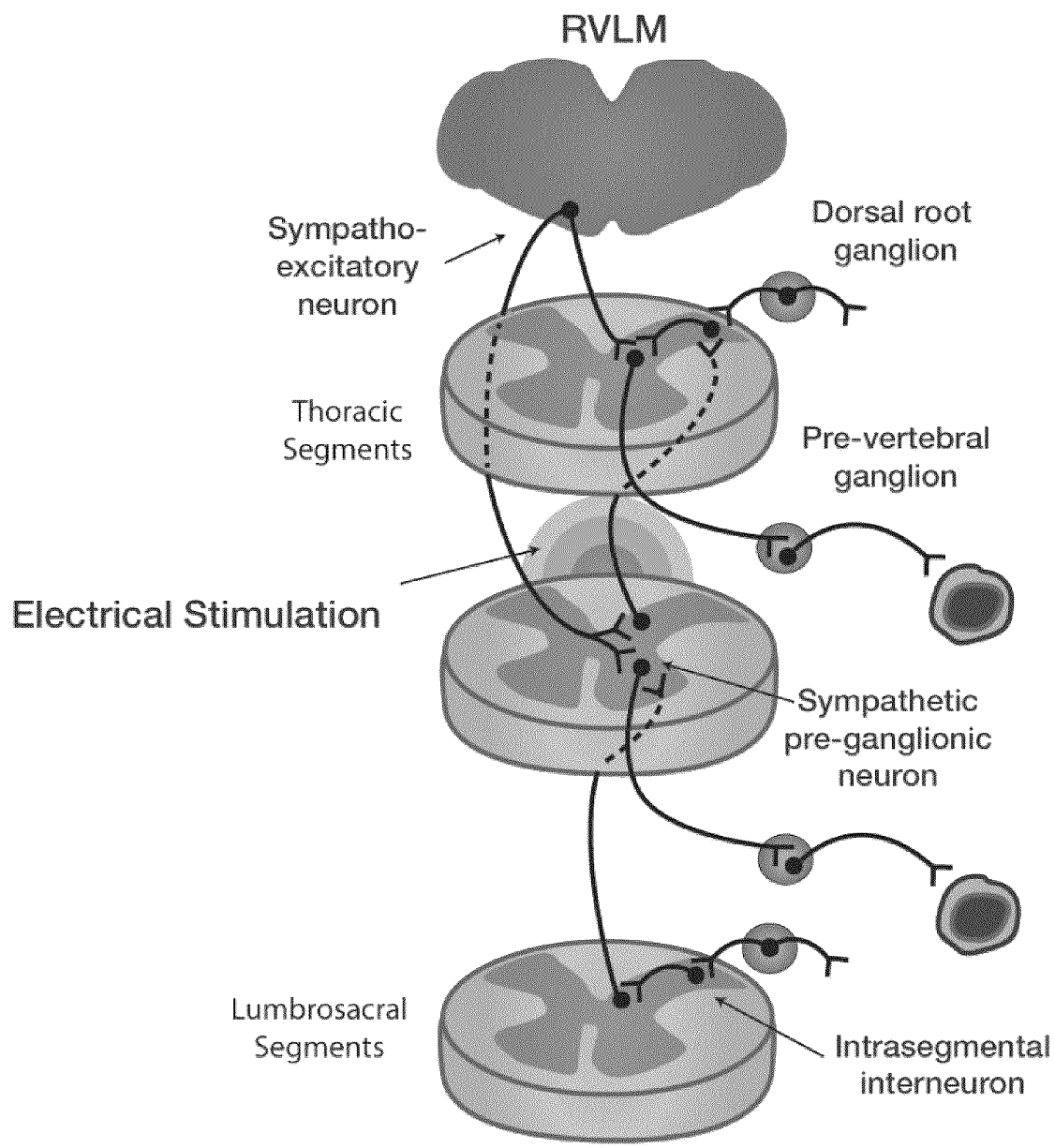
FIG. 7 illustrates a theoretical framework of transcutaneous stimulation.

Example 2: Cardiovascular Optimized Epidural Stimulation Improved Multiple Facets of Cardiovascular Function in All Three Study Participants FIG. 4 illustrates the improvements to cardiovascular function following controlled electrical stimulation in individuals with SCI. FIGS. 4A to 4C are enlarged views of portions of FIG. 4. FIG. 4A shows Systolic blood pressure (SBP), posterior cerebral artery velocity (PCA), and mid cerebral artery (MCA) velocity were all maintained with stimulation in response to a 10 minute sit-up test. Stimulation increased low-frequency oscillations in SBP while in the seated position, indicating a return of supraspinal cardiovascular control. FIG. 4 (top right) shows changes in posterior cerebral artery blood flow in response to neural activation using a classical eyes-closed eyes-open task indicate that stimulation restored neurovascular coupling in all individuals (i.e., there was an appropriate increase in PCA flow in response to neural activation with stimulation), which was virtually absent without stimulation. FIG. 4C shows: echocardiography-derived cardiac responses to orthostatic challenge indicate that stimulation prevented the decline in end-diastolic volume (EDV), stroke volume (SV) and cardiac output (CO) noted without stimulation; consequently, there was also a reduction in the magnitude of orthostatic-induced tachycardia with stimulation. Also shown are the group mean±SD for the major cardiac variables summarized in panel Example 3: Theoretical Restoration of Dormant Supraspinal Descending Sympathetic Cardiovascular Pathways Through Potentiation of Caudal Sympathetic Circuitry FIGS. 5A to 5C show how cardiovascular functioning may be restored in individuals with SCI following controlled electrical stimulation. FIG. 5A shows descending sympathetic pathways from the rostral ventrolateral medulla (RVLM) in an intact spinal cord may lead to efficacious action potentials (i.e., depolarization) in sympathetic circuitry that allow for supraspinal control over vascular tone (i.e., vasoconstriction) and blood pressure. FIG. 5B shows how interrupted descending sympathetic pathways due to an anatomically discomplete SCI, where a small number of preserved descending sympathetic fibres crossing the site of injury are not capable of eliciting action potentials in sympathetic circuitry caudal to injury. FIG. 5C illustrates that epidural spinal electrical stimulation increases the resting membrane potential of sympathetic circuity caudal to the spinal cord injury allowing for the previously non-efficacious preserved descending sympathetic fibres crossing the site of injury to actively regulate caudal sympathetic circuits, and thereby restore supraspinal control of vascular tone and blood pressure. As shown in FIG. 7, epidural electrical stimulation may stimulate dorsal afferents that likely affect the membrane potential of intersegmental and intrasegmental neurons, that: 1) receive direct input from descending sympathetic pathways, and 2) directly and indirectly lead to depolarization of sympathetic preganglionic neurons leading to regulation of vascular tone.

Figure 6:
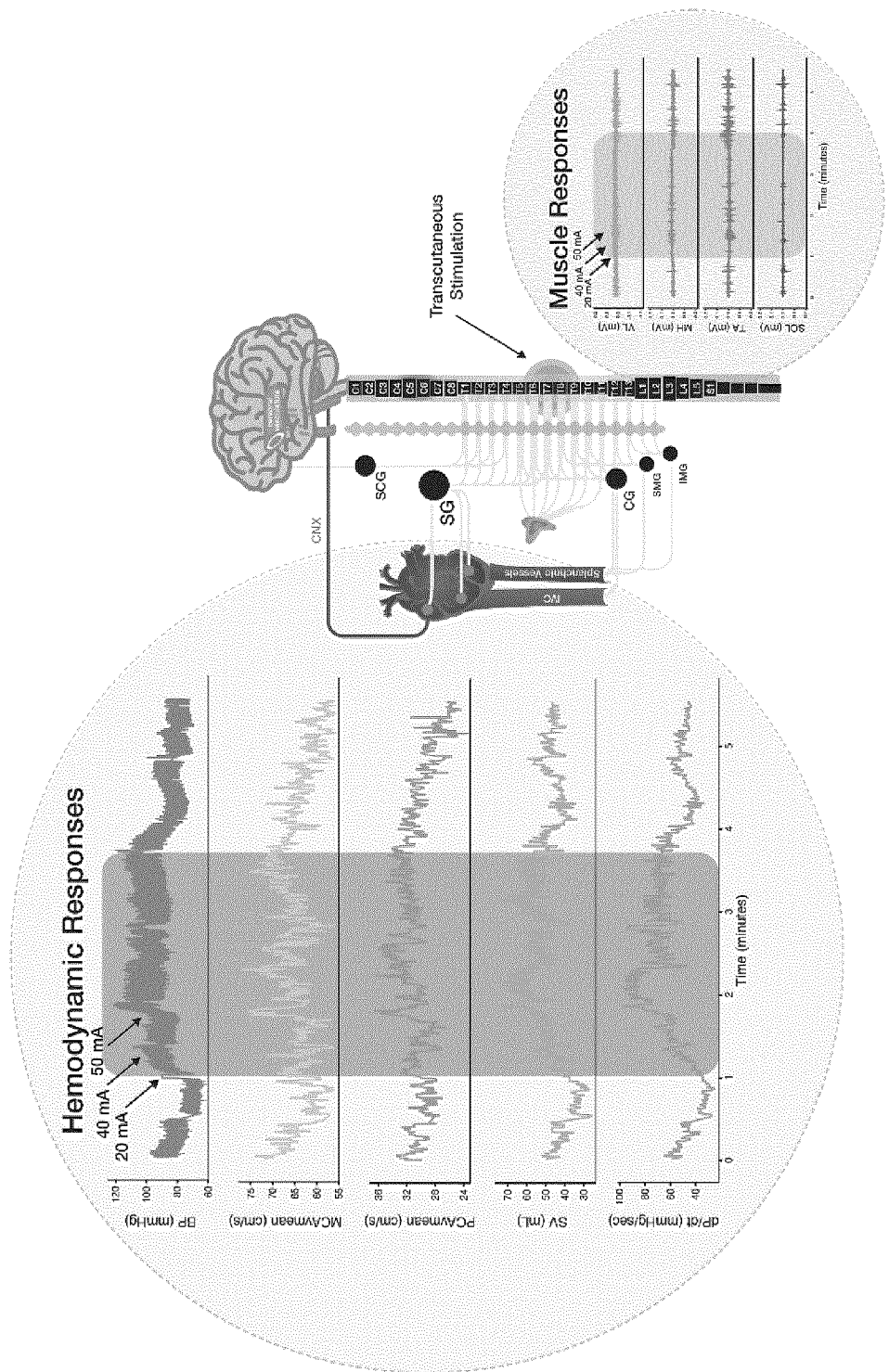
FIG. 6 illustrates improved integrated cardiovascular responses to orthostatic challenge in an individual resulting from thoracic electrical stimulation.

Example 6: Thoracic Electrical Transcutaneous Stimulation Improved Integrated Cardiovascular Responses to Orthostatic Challenge FIG. 6 shows improvements to cardiovascular function following controlled transcutaneous electrical stimulation in an individual with SCI. Participant: Female, 32 years of age, spinal cord injury at C6 (AIS-A), injured August 2009. Left Inlet: Although suffering from severe orthostatic hypotension when assuming upright posture, electrical stimulation at the TVII level restored blood pressure, cerebral blood flow, cardiac function, and symptoms of orthostatic intolerance to supine levels. Note: Increasing current (from 20 mA, to 40 mA, to 50 mA) resulted in step-wise increases in cardiovascular function. Right Inlet: electromyography recording of lower-limbs shows that skeletal muscle contraction was not activating the skeletal muscle pump of the venous vasculature, indicating that excitation of sympathetic preganglionic neurons was responsible for the cardiovascular restoration. Note: Without stimulation self-reported symptoms of presyncope were severe, being between 6-9, while with stimulation symptoms were completely abrogated. Participant reported that cognitive processing was so slow in the upright position that she was "not conversational" until the stimulation was turned on.

Example 7: Theoretical Framework of Transcutaneous Stimulation

FIG. 7 shows how thoracic level stimulation using transcutaneous electrical stimulation excites dorsal afferents that likely excite intersegmental and intrasegmental neurons, which directly and indirectly lead to depolarization of sympathetic preganglionic neurons leading to increased vascular tone.

Interpretation of Terms

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

The following abbreviations have the following meanings:
  BP, blood pressure.
  CG, celiac ganglia
  CO, cardiac output.
  DBP, diastolic blood pressure.
  dP/dt, delta pressure over delta time (cardiac contractility).
  EDV end-diastolic volume.
  HR, heart rate.
  IMG, inferior mesenteric ganglia.
  MCA mid cerebral artery.
  MH, medial hamstring.
  PCA, posterior cerebral artery.
  PCAvmean, mean flow velocity for PCA.
  RVLM, rostral ventrolateral medulla.
  SBP, systolic blood pressure.
  SCG, superior cervical ganglia.

SCI, spinal cord injury.
SG, stellate ganglia.
SMG, superior mesenteric ganglia.
SOL, soleus.
SV, stroke volume.
TA, tibialis anterior.
VL, vastus lateralis.
vmean, mean flow velocity.

The invention may also be provided in the form of a program product. The program product may comprise any non-transitory medium which carries a set of computer-readable instructions which, when executed by a data processor, cause the data processor to execute a method of the invention (e.g. a method as illustrated in FIG. 2 or FIG. 2A). Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Various features are described herein as being present in "some embodiments". Such features are not mandatory and may not be present in all embodiments. Embodiments of the invention may include zero, any one or any combination of two or more of such features. This is limited only to the extent that certain ones of such features may be incompatible with other ones of such features in the sense that it would be impossible for a person of ordinary skill in the art to construct a practical embodiment that combines such incompatible features. Consequently, separate or combined statements in the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for managing blood pressure lability in a patient suffering from spinal cord injury (SCI), the method comprising:
   monitoring a blood pressure of the patient and providing a BP signal representative of the blood pressure of the patient;
   based on the BP signal, applying stimulation to tissues of the patient's lower back caudal to the SCI wherein the method comprises:
      increasing a level of the stimulation if the BP signal indicates that the patient's blood pressure is below the target range,
      decreasing the level of the stimulation if the if the BP signal indicates that the patient's blood pressure is above the target range; and
      maintaining the level of the stimulation if the if the BP signal indicates that the patient's blood pressure is within the target range.

2. The method according to claim 1 comprising, after setting a level of the stimulation, waiting for at least a lag duration before adjusting the level of the stimulation again.

3. The method according to claim 2 wherein the lag duration is in the range of a few seconds to 15 minutes.

4. The method according to claim 3 comprising processing the BP signal to yield a stimulation control signal and applying the stimulation control signal to control a pulse generator that is connected to apply a stimulation signal to tissues in the patient's lower back by way of electrodes of an implanted or transdermal electrode array wherein the electrodes are caudal to the SCI.

5. The method according to claim 1 wherein monitoring the blood pressure comprises determining an average blood pressure for a period having a length of a few seconds to a few minutes.

6. The method according to claim 1 wherein the stimulation is electrical stimulation.

7. The method according to claim 6 comprising delivering the electrical stimulation to the dorsal aspect of the spinal cord of the patient.

8. The method according to claim 7 comprising delivering the electrical stimulation by an implanted electrode structure.

9. The method according to claim 8 wherein the electrode structure is located over lumbosacral spinal cord segments of the patient's spine.

10. The method according to claim 7 comprising, by the stimulation, stimulating dorsal roots, dorsal afferent fibres and/or intraspinal structures that are connected directly or indirectly to sympathetic preganglionic neurons that affect the patient's blood pressure.

11. The method according to claim 7 comprising, by the stimulation, causing signals on efferent nerves that affect the patient's blood pressure.

12. The method according to claim 7 wherein the stimulation comprises electrical pulses presented at a pulse frequency in the range of about 5 Hz to 10 kHz.

13. The method according to claim 7 wherein the stimulation comprises a continuous series of electrical pulses, the pulses having pulse widths in the range of about 0.002 seconds to about 20 seconds.

14. The method according to claim 7 wherein the stimulation has a voltage in the range of about 0.1 V to about 24 V.

15. The method according to claim 7 wherein the stimulation has an amperage in the range of about 0 mA to about 1000 mA.

16. The method according to claim 6 comprising delivering the electrical stimulation transdermally.

17. The method according to claim 6 wherein increasing the level of stimulation comprises increasing a voltage of the stimulation and decreasing the level of the stimulation comprises decreasing the voltage of the stimulation.

18. The method according to claim 17 wherein increasing the level of stimulation comprises incrementally raising the voltage of the stimulation by increments having sizes in the range of 0.1 V to 10 V.

19. The method according to claim 6 wherein increasing the level of stimulation comprises increasing an electrical current of the electrical stimulation.

20. The method according to claim 19 wherein increasing the level of stimulation comprises incrementally increasing the electrical current of the stimulation in increments in the range of about 0.1 mA to about 150 mA.

21. The method according to claim 1 comprising limiting the stimulation to be below a level that causes spasticity in the patient.

22. The method according to claim 1 comprising setting the target range based upon a user input.

23. The method according to claim 1 comprising automatically setting the target range based upon a time of day.

24. The method according to claim 1 comprising inhibiting increasing the level of the stimulation in response to receiving a "STOP" command issued in response to activation of a user control.

25. The method according to claim 1 further comprising administering to the patient a pharmacological agent that is effective to increase blood pressure.

26. The method according to claim 1 further comprising regulating function of the patient's bladder and/or bowel by delivering alternative stimulation selected to facilitate urination and/or bowel function without significantly affecting blood the patient's pressure.

27. The method according to claim 26 wherein each of the stimulation and the alternative stimulation comprises electrical stimulation, the stimulation is provided by a first set of electrodes and the alternative stimulation is provided by a second set of electrodes.

28. The method according to claim 26 comprising temporarily suspending control over the patient's blood pressure while delivering the alternative stimulation.

* * * * *